US012590291B2

(12) United States Patent
Kawarai et al.

(10) Patent No.: US 12,590,291 B2
(45) Date of Patent: Mar. 31, 2026

(54) METHOD OF INDUCING EXPRESSION OF CALCIUM CHANNEL AND/OR CALCIUM PUMP, AND APPARATUS THEREFOR

(71) Applicant: Nichia Corporation, Anan (JP)

(72) Inventors: Shinpei Kawarai, Sagamihara (JP); Atsushi Tsukamoto, Sagamihara (JP); Yasuo Fujikawa, Yokohama (JP); Tomohiro Tsurumoto, Yokohama (JP)

(73) Assignee: NICHIA CORPORATION, Anan (JP)

( * ) Notice: Subject to any disclaimer, the term of this patent is extended or adjusted under 35 U.S.C. 154(b) by 846 days.

(21) Appl. No.: 17/729,752

(22) Filed: Apr. 26, 2022

(65) Prior Publication Data

US 2022/0340872 A1      Oct. 27, 2022

(30) Foreign Application Priority Data

Apr. 27, 2021      (JP) ................................. 2021-075131

(51) Int. Cl.
| | |
|---|---|
| *C12N 5/071* | (2010.01) |
| *C12M 1/00* | (2006.01) |
| *C12M 1/22* | (2006.01) |
| *C12M 3/00* | (2006.01) |
| *C12Q 1/6851* | (2018.01) |
| *C12Q 1/6876* | (2018.01) |
| *G01N 33/50* | (2006.01) |

(52) U.S. Cl.
CPC ........... *C12N 5/0629* (2013.01); *C12M 21/02* (2013.01); *C12M 23/10* (2013.01); *C12M 23/44* (2013.01); *C12Q 1/6876* (2013.01); *G01N 33/5023* (2013.01); *C12Q 1/6851* (2013.01)

(58) Field of Classification Search
CPC ......................... C12N 5/0629; C12N 2529/10; C12N 5/0062; C12M 21/02; C12M 23/10; C12M 23/44; C12M 31/02; C12M 35/02; C12M 41/06; C12Q 1/6876; C12Q 1/6851; G01N 33/5023
See application file for complete search history.

(56) References Cited

U.S. PATENT DOCUMENTS

| | | |
|---|---|---|
| 6,248,790 B1 | 6/2001 | Uckun et al. |
| 2007/0164233 A1 | 7/2007 | Mohr |
| 2013/0243711 A1 | 9/2013 | Chung et al. |

FOREIGN PATENT DOCUMENTS

| | | |
|---|---|---|
| JP | 2009-520703 A | 5/2009 |
| JP | 2009-524425 A | 7/2009 |
| JP | 2015-515455 A | 5/2015 |
| JP | 2021-508539 A | 3/2021 |
| WO | WO-2007/076832 A1 | 7/2007 |
| WO | WO-2007/086637 A1 | 8/2007 |
| WO | WO-2013/137505 A1 | 9/2013 |
| WO | WO-2019/133929 A1 | 7/2019 |

OTHER PUBLICATIONS

Diode (May 15, 2019 according to wayback machine, https://www.photonics.com/Articles/Light-Emitting_Diodes_A_Primer/a36706, examiner cited) {herein Diode}. (Year: 2019).*
Suda et l (1993, Transfusion, examiner cited) {herein Suda} (Year: 1993).*
Mendez et al (1998, J Physiol, examiner cited) {herein Mendez) (Year: 1998).*
Shi et at (2012, Technical Reports, examiner cited) {herein Shi}. (Year: 2012).*
Edmund (Wayback Machine Date: Dec. 2, 2022, https://www.edmundoptics.com/p/320nm-cwl-125mm-dia-hard-coated-od-4-10nm-bandpass-filter/33100/#:~: text=Optical%20Properties,200%20%2D%201200, Examiner cited) {herein Edmund}. (Year: 2022).*
Maeda Yusuke, Bachelor Thesis—"Preliminary Study of Narrow band UVB Therapy in Dogs", Azabu University, Faculty of Veterinary Medicine, Department of Veterinary Medicine, Animal Science, V15007.
G Bart et al., "rClca2 is associated with epidermal differentiation and is strongly downregulated by ultraviolet radiation", The British Journal of Dermatology, 2014, vol. 171, pp. 376-387.
Leena Rauhala et al., "Low Dose Ultraviolet B Irradiation Increases Hyaluronan Synthesis in Epidermal Keratinocytes via Sequential Induction of Hyaluronan Synthases Has1-3 Mediated by p38 and Ca2/Calmodulin-dependent Protein Kinase II (CaMKII) Signaling", The Journal of Biological Chemistry, 2013, vol. 288, No. 25, p. 17999-18012.
Yao Shen et al., "Transcriptome Analysis Identifies the Dysregulation of Ultraviolet Target Genes in Human Skin Cancers", PLOS/ONE, 2016, DOI: 10.1371/journal.pone.0163054.

* cited by examiner

*Primary Examiner* — Manjunath N Rao
*Assistant Examiner* — Erica Nicole Jones-Foster
(74) *Attorney, Agent, or Firm* — Foley & Lardner LLP

(57)      ABSTRACT

A method of inducing expression of a calcium channel and/or a calcium pump in a cell includes: irradiating the cell with light in a wavelength range of 315-325 nm. The calcium channel and/or the calcium pump is/are at least one selected from the group consisting of dihydropyridine receptor (DHPR), voltage-gated calcium channel (VGCC), ryanodine receptor (RYR), and sarcoendoplasmic reticulum $Ca^{2+}$-ATPase (SERCA).

10 Claims, 8 Drawing Sheets

DHPR・VGCC (gene name：CACNG1)

DHPR・VGCC (gene name：CACNG6)

CASQ (gene name : CASQ2)

HRC (gene name : HRC)

METHOD OF INDUCING EXPRESSION OF CALCIUM CHANNEL AND/OR CALCIUM PUMP, AND APPARATUS THEREFOR

CROSS-SECTION TO RELATED APPLICATIONS

This application claims priority under 35 USC § 119 to Japanese Patent Application No. 2021-075131, filed on Apr. 27, 2021, the contents of which are incorporated herein by reference in their entirety.

BACKGROUND

The present disclosure relates to a method of inducing expression of a calcium channel and/or a calcium pump.

Japanese Patent Application KOHYO Publication No. 2015-515455 relates to a TRPV1 inhibitory peptide, which inhibits the expression of UV exposure-induced MMP (matrix metalloproteinase) and pro-inflammatory cytokine and inhibits intracellular Ca2+ uptake and increases in skin thickness, and to an anti-skin aging or anti-skin wrinkle composition comprising the peptide. The document describes the irradiation of mouse skin with broadband UV light from a fluorescent sunlamp with an emission spectrum between 275 and 380 nm.

Calcium ion ($Ca^{2+}$) is an intracellular signaling agent, which regulates various biological processes such as proliferation, differentiation, gene expression, exocytosis (e.g., release of hormones, cytokines, or neurotransmitters), apoptosis, muscle contraction and metabolism. Intracellular calcium ion levels are normally maintained in the range of 10 to 100 nM, and certain stimulation can increase the levels to 100 to 200 nM. The influx of calcium ions into the cytoplasm is via calcium (ion) channels and nonselective cation channels, and the efflux is mediated by calcium pumps.

SUMMARY

Accordingly, there are needs to prove a technique for inducing expression of a calcium channel and/or a calcium pump that calcium ions selectively permeate, because it is very useful to control, regulate or investigate various biological events or phenomena.

According to one embodiment of the present disclosure, a method of inducing expression of a calcium channel and/or a calcium pump in a cell includes a step of irradiating the cell with light in a wavelength range of 315-325 nm, wherein the calcium channel and/or the calcium pump is/are at least one selected from the group consisting of dihydropyridine receptor (DIPR), voltage-gated calcium channel (VGCC), ryanodine receptor (RYR), and sarcoendoplasmic reticulum $Ca^{2+}$-ATPase (SERCA).

According to another embodiment of the present disclosure, an apparatus for culturing a cell includes: a first irradiation unit configured to mainly emit light in a wavelength range of 315-325 nm; a first mounting unit configured to support a cell culture vessel and located within an irradiation area of the first irradiation unit; a first irradiation control unit configured to control the first irradiation unit; and a housing configured to accommodate the first irradiation unit and the first mounting unit therein.

According to a method of the present disclosure, a calcium channel and/or a calcium pump can be induced to be expressed in a cell.

According to an apparatus of the present disclosure, a calcium channel and/or a calcium pump can be easily or conveniently induced to be expressed in a cell.

DETAILED DESCRIPTION

Figure 1:
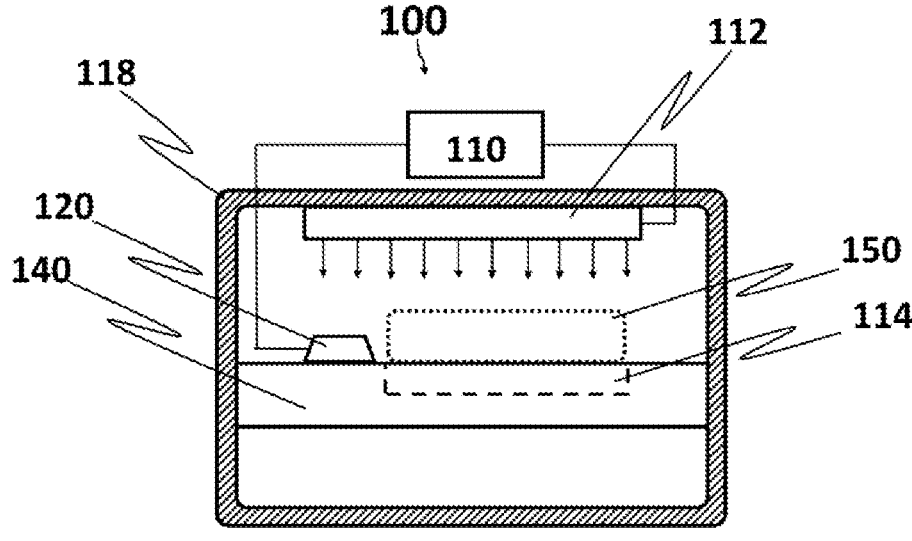
FIG. 1 illustrates Embodiment 1 of an apparatus according to the present disclosure.

Unless defined otherwise, all technical and scientific terms used herein have the same meaning as is commonly understood by one of ordinary skill in the art to which the present disclosure pertains. Although any apparatuses, devices, methods, and materials similar or equivalent to those described herein can be used in the practice or testing of the present disclosure, representative apparatuses, devices, methods, and materials are now described.

As used herein and the appended claims, the singular forms "a," "an," and "the" include plural referents unless the context clearly dictates otherwise. The terms "comprise," "comprising," "include," "including," "have," "has," "having," and the like are intended to be inclusive and mean that there may be additional elements other than the listed elements.

As used herein, a numerical range "a to b" or "a-b" ("a" and "b" representing specific numerical values) means the range including both of the values "a" and "b," that is, the range "between a and b, both inclusive."

<Method of Inducing Expression of a Calcium Channel and/or a Calcium Pump>

An aspect of the present disclosure provides a method of inducing expression of a calcium channel and/or a calcium pump in a cell, the method comprising irradiating the cell with light in a wavelength range of 315-325 nm, wherein the calcium channel and/or the calcium pump is/are at least one selected from the group consisting of dihydropyridine receptor (DHPR), voltage-gated calcium channel (VGCC), ryanodine receptor (RYR), and sarcoendoplasmic reticulum $Ca^{2+}$-ATPase (SERCA).

The light in the wavelength range of 315-325 nm is irradiated to the cell in an effective amount to induce expression of a calcium channel and/or a calcium pump in the irradiated cell.

In the present disclosure, inducing expression of a calcium channel and/or a calcium pump includes upregulating expression of the calcium channel and/or the calcium pump.

In the present disclosure, "inducing expression" or "induction of expression" refers to an increase, such as 20-fold or more increase, more particularly 30-fold or more increase, more particularly 40-fold or more increase, more particularly 50-fold or more increase, more particularly 60-fold or more increase, more particularly 70-fold or more increase, and more particularly 80-fold or more increase, in the expression level of a calcium channel and/or a calcium pump of interest, compared to the level in the cell before the light irradiation according to the present disclosure (which cell is identical to the irradiated cell) or a cell not irradiated according to the present disclosure (which cell is different from the irradiated cell).

In the present disclosure, the term "calcium channel" refers to dihydropyridine receptor (DHPR), voltage-gated calcium channel (VGCC), and/or ryanodine receptor (RYR), unless the context clearly dictates otherwise. Voltage-gated calcium channels include L-type channels, non-L-type (N-type, P/Q-type, or R-type) channels, T-type channels, and the like, and preferably may be L-type channels. Ryanodine receptors include ryanodine receptor 1 (RYR1) and ryanodine receptor 2 (RYR2). Induced expression of calcium channels facilitates the entry of calcium ions into the cytoplasm from the extracellular environment or the endoplasmic reticulum, thus increasing the influx of calcium ions In the present disclosure, the term "calcium pump" refers to sarcoendoplasmic reticulum $Ca^{2+}$-ATPase (SERCA), unless the context clearly dictates otherwise. Induced expression of SERCA facilitates the exit of calcium ions from the cytoplasm, thus increasing the efflux of calcium ions The lower limit of the fluence of the light in the wavelength range of 315-325 nm irradiated to the cell may be, for example, 10 mJ/cm², 50 mJ/cm², 100 mJ/cm², 200 mJ/cm², 300 mJ/cm², 400 mJ/cm², or 500 mJ/cm², and the upper limit may be, for example, 5000 mJ/cm², 4500 mJ/cm², 4000 mJ/cm², 3500 mJ/cm², 3000 mJ/cm², 2500 mJ/cm², 2000 mJ/cm², or 1500 mJ/cm². Where the fluence of the light in the wavelength range of 315-325 nm is less than 15 mJ/cm², it is believed to be likely that the induction of expression of calcium channel and/or calcium pump may not be achieved. Where the fluence is greater than 5000 mJ/cm², it is believed to be likely that the cell is largely damaged and therefore the induction of expression of calcium channel and/or calcium pump may not be achieved.

A particular fluence of the light in the wavelength range of 315-325 nm irradiated to the cell may be in a range of between a lower limit value and an upper limit value, wherein the lower limit value is selected from the above-mentioned lower limit values and the upper limit value is selected from the above-mentioned upper limit values. Specific examples of the fluence range include, but not limited to, 10-5000 mJ/cm², in particular 50-4500 mJ/cm², 100-4000 mJ/cm², 200-3500 mJ/cm², 300-3000 mJ/cm², 400-2500 mJ/cm², 500-2000 mJ/cm², and 500-1500 mJ/cm².

The light in the wavelength range of 315-325 nm may be irradiated to the same cell once, or two or more times. In the case in which the light in the wavelength range of 315-325 nm is irradiated two or more times, a total fluence for each irradiation may be in a range of between any one of the above-mentioned lower limit values and any one of the above-mentioned upper limit values. The lower limit of fluence for each irradiation may be, for example, 5 mJ/cm², 10 mJ/cm², 20 mJ/cm², 25 mJ/cm², 50 mJ/cm², 100 mJ/cm², 150 mJ/cm², 200 mJ/cm², or 250 mJ/cm². The upper limit may be, for example, 2500 mJ/cm², 2000 mJ/cm², 1500 mJ/cm², 1000 mJ/cm², 750 mJ/cm², 500 mJ/cm², or 300 mJ/cm². In the case of two or more irradiations, the number of irradiations may be, for example 2 to 10, more specifically, 2 to 8, 2 to 6, or 2 to 4, and the irradiation interval may be, for example once every 1 to 48 hours, more specifically, once every 3 hours, once every 4 hours, once every 6 hours, once every 12 hours, once every 24 hours (a day), or once every 48 hours.

The maximum absorption wavelength of DNA and RNA is around 260 nm and proteins can absorb light at around 200 nm and around 280 nm. Therefore, it is concerned that light at around 200-280 nm may have a noticeable adverse effect to plants. Therefore, it is preferable if light in the range of 200-300 nm, more preferably 200-310 nm, and more preferably 200-315 nm is irradiated to the cell of interest at a fluence that is less than 50%, more preferably less than 40%, more preferably less than 30%, more preferably less than 20%, more preferably less than 15%, more preferably less than 10%, more preferably less than 5%, and more preferably less than 1%, of the fluence of the light in the wavelength range of 315-325 nm, or it is not irradiated to the cell (that is, its fluence is 0% of that of the light in the wavelength range of 315-325 nm).

It is believed that light in the wavelength range of 300-400 nm does not contribute to induce expression of a calcium channel and/or a calcium pump in cells and, what is worse, causes damage to cells. Therefore, the irradiation at a fluence in the wavelength range of 330-400 nm that is 50% or more of the fluence in the wavelength range of 315-325 nm cannot efficiently achieve the said expression induction. In view of avoiding an adverse effect to the cell and energy efficiency, it is preferable if light in the range of 330-400 nm is irradiated to the cell of interest at a fluence that is less than 50%, more preferably less than 40%, more preferably less than 30%, more preferably less than 20%, more preferably less than 15%, more preferably less than 10%, more preferably less than 5%, and more preferably less than 1%, of the fluence of the light in the wavelength range of 315-325 nm, or it is not irradiated to the cell (that is, its fluence is 0% of that of the light in the wavelength range of 315-325 nm).

The light in the wavelength range of 315-325 nm is irradiated to the cell at an irradiance (or fluence rate), for example, in a range of 0.1-300 mW/cm². It is likely that irradiation at an irradiance of less than 0.1 mW/cm² may not efficiently induce expression of calcium channel and/or calcium pump in the cell. It is likely that irradiation at an irradiance of more than 300 mW/cm² may cause damage to the cell. More particularly, the light in the wavelength range of 315-325 nm is irradiated to the cell in a range of 0.5-200 mW/cm², more particularly 1-100 mW/cm², more particularly 5-50 mW/cm², and more particularly 5-20 mW/cm². In the present disclosure, the "irradiance" is an amount at the level of the cell of interest to be irradiated.

In the case in which the cell is from or in a tissue, such as skin, that is constantly exposed to ultraviolet light, it is possible to increase the irradiance to, for example, at or near 300 mW/cm² to complete the irradiation to the cell at a specified fluence in a shorter time. In the case in which the cell is from mucosa or an internal organ, or in a cell culture, in which cells are grown in an artificial environment, the cell is sensitive to intense UV light and therefore it is preferable to irradiate the cell at a lower irradiance of 0.1 mW/cm², for example, in a longer time.

In the present disclosure, the light to be irradiated to the cell includes light in a wavelength range of 315-325 nm, and more specifically has the main peak wavelength in a range of 315-325 nm. Irradiation of such a light to the cell can induce expression of a calcium channel and/or a calcium pump in the cell. The wavelength range, the intensity spectrum, the main peak wavelength and the full width at half maximum (FWHM) can be determined by any of the techniques known in the art, for example, on a spectrometer. As used herein, the term "main peak wavelength" refers to the peak wavelength at which the intensity is the maximum in its spectrum. In the context of light having a single peak, such as LED light, the term "peak wavelength" is synonymous with "main peak wavelength."

It is preferable if the light in the wavelength range of 315-325 nm is irradiated simultaneously to two or more cells. In other words, the irradiation area of the light in the wavelength range of 315-325 nm preferably includes two or more cells. The lower limit of the irradiation area of the light in the wavelength range of 315-325 nm may be, for example, 0.1 cm², 0.2 cm², 0.5 cm², 1 cm², 2 cm², 5 cm², 10 cm², 20 cm², 50 cm², 100 cm², 200 cm², or 500 cm². The upper limit may by, for example, 10000 cm², 5000 cm², 3000 cm², or 1000 cm².

A particular irradiation area of the light in the wavelength range of 315-325 nm may be in a range of between a lower limit value and an upper limit value, wherein the lower limit value is selected from the above-mentioned lower limit values and the upper limit value is selected from the above-mentioned upper limit values. Specific examples of the irradiation area include, but not limited to, 1-10000 cm², more specifically 5-10000 cm², more specifically 10-10000 cm², more specifically 20-1000 cm², more specifically 20-10000 cm², more specifically 20-5000 cm², more specifically 20-3000 cm², and more specifically 50-3000 cm².

The light in the wavelength range of 315-325 nm may be or include an artificial light. As used herein, the term "artificial light" refers to light emitted by an artificial light source, and a light component of certain wavelengths extracted, by using an optical filter, for example, from natural light (mostly sunlight).

Artificial light sources are not particularly limited so long as they are configured to emit the light in the wavelength range of 315-325 nm, and include, for example, light-emitting diodes (LEDs), laser diodes (LDs), xenon lamps, fluorescent lamps, incandescent lamps, metal hydride lamps, high-pressure sodium lamps, and the like.

In the case in which the light source used emits, in addition to the light in the wavelength range of 315-325 nm, the light in a wavelength range of 200-300 nm (or in a wavelength range of 200-310 nm) at a radiant intensity that is 50% or more of that of the light in the wavelength range of 315-325 nm, a filter may be used with the light source, having a transmittance to the light in the wavelength range of 315-325 nm higher than that of the light in the wavelength range of 200-300 nm (or 200-310 nm), so that the light in the wavelength range of 200-300 nm (or 200-310 nm) is irradiated to the cell of interest at a fluence or an irradiance that is less than 20%, more particularly less than 15%, less than 10%, less than 5% or less than 1%, of that of the light in the wavelength range of 315-325 nm.

Additionally or alternatively, in the case in which the light source used emits, in addition to the light in the wavelength range of 315-325 nm, the light in a wavelength range of 330-400 nm at a radiant intensity that is 50% or more of that of the light in the wavelength range of 315-325 nm, a filter may be used with the light source, having a transmittance to the light in the wavelength range of 315-325 nm higher than that of the light in the wavelength range of 330-400 nm, so that the light in the wavelength range of 330-400 nm is irradiated to the cell of interest at a fluence or an irradiance that is less than 20%, more particularly less than 15%, less than 10%, less than 5% or less than 1%, of that of the light in the wavelength range of 315-325 nm.

In view of energy efficiency, the irradiated light in the wavelength range of 315-325 nm preferably has a wavelength spectrum having the main peak wavelength at 320±5 nm, more preferably at 320±4 nm, more preferably at 320±3 nm, and more preferably at 320±2 nm. Preferably, the irradiated light does not have a second peak, that is, it has a single peak in its emission spectrum, or it has a second peak whose intensity is one-tenth (1/10) or less of that of the main peak.

The full width at half maximum (FWHM) of the main peak is, for example, in a range from 1 to 20 nm, preferably 1 to 15 nm, more preferably 1 to 10 nm, and more preferably 1 to 5 nm. By use of light having a main peak with a full width at half maximum of 20 nm or less, the cell can be irradiated with light in a wavelength range that is effective in inducing expression of a calcium channel and/or a calcium pump, while avoiding irradiation with light in a wavelength range that does not contribute to the expression induction, and achieve a further increased energy efficiency. It is also possible to use light having a main peak with a full width at half maximum of less than 1 nm by cutting off the light in the unnecessary wavelength range with, for example, a filter. In view of cost performance, however, currently it is preferable to use light having a main peak with a full width at half maximum of 1 nm or more. In some preferred embodiment, the light irradiated to the cell has a wavelength spectrum having a peak wavelength at 320±5 nm, and more particularly 320±3 nm, with a full width at half maximum in a range of 1-20 nm, more particularly 1-10 nm, more particularly 1-5 nm.

A particularly preferable light source of the light to be irradiated to the cell is a light-emitting diode (LED), or a laser diode (LD). An LED configured to emit light in the wavelength range of 315-325 nm can be formed of, for example, an AlGaN- or InAlGaN-based material.

The use of an LED or LD as a light source can easily achieve selective irradiation with light in a wavelength range effective in inducing expression of a calcium channel and/or a calcium pump in the cell, while avoiding irradiation with light in a wavelength range that does not contribute to the expression induction. In view of energy efficiency and economic efficiency, use of LED or LD is preferable due to the energy concentration, low heat generation, low power consumption and long life. In addition, the fluence (or irradiation dose) and/or irradiance can be easily controlled or managed. Furthermore, use of LED or LD can irradiate only a cell(s) in a necessary area on the plane (a target cell(s)) and therefore reduce or prevent the effect of the light on other cells surrounding the target cell(s).

In the case in which the light in the wavelength range of 315-325 nm is a laser light, the light may be irradiated in combination with one or more laser lights at other wavelengths (e.g., laser light at around 640 nm and/or around 960 nm). The combined irradiation makes it possible to irradiate cells inside (in a deep portion of) layered cells without significantly affecting the superficial cells by using multiphoton (two-photon, three-photon, four- or more photon) absorption phenomenon.

It is possible to irradiate the cell(s) in vivo by using an implantable optical device, endoscope or catheter.

The light in the wavelength range of 315-325 nm may be irradiated to the cell under irradiation of light from a light source other than the light source emitting the light in the wavelength range of 315-325 nm (including natural light). In a mixed or composite light of the light from the light source emitting the light in the wavelength range of 315-325 nm with the light from the light source other than the light source emitting the light in the wavelength range of 315-325 nm, the fluence or irradiance of the light in the wavelength range of 200-300 nm (or 200-310 nm) is preferably less than 20%, more preferably less than 15%, more preferably less than 10%, more preferably less than 5%, and more preferably less than 1%, of the fluence or irradiance, respectively, of the light in the wavelength range of 315-325 nm. In the mixed or composite light, the fluence or irradiance of the light in the wavelength range of 330-400 nm is preferably is less than 50%, more preferably less than 40%, more preferably less than 30%, more preferably less than 25%, more preferably less than 20%, more preferably less than 15%, more preferably less than 10%, more preferably less than 5%, and more preferably less than 1%, of the fluence or irradiance, respectively, of the light in the wavelength range of 315-325 nm.

The fluence of the light in the wavelength range of 315-325 nm to the cell may be adjusted by controlling switching on and off the light source that emits the light in the wavelength range of 315-325 nm at a constant radiant intensity (i.e., controlling light-on time), or by controlling the radiant intensity of the light in the wavelength range of 315-325 nm whose light source lights on in a constant time duration, or by controlling the radiant intensity of the light in the wavelength range of 315-325 nm as well as switching on and off its light source. The fluence of the light in the wavelength range of 315-325 nm to the cell may be measured with a sensor, in particular luminance sensor, provided near the cell to be irradiated, and further may be regulated as described above according to the output of the sensor.

The light in the range of 315-325 nm may be irradiated to the cell as continuous light or intermittent light (such as pulsed light), or a combination thereof. Preferably, the light in the range of 315-325 nm may be irradiated as intermittent light. The use of intermittent light can avoid or reduce a rise in temperature of the irradiated cell and/or the light source emitting the light. Specific examples of intermittent light include pulsed light having a pulse width of 100 ms or less, more specifically 50 ms or less, more specifically 20 ms or less, more specifically 10 ms or less, and more specifically 5 ms or less, and a duty ratio of 50% or less, more specifically 40% or less, more specifically 30% or less, more specifically 20% or less, more specifically 10% or less, and more particularly 5% or less.

Preferable, the light in the wavelength range of 315-325 nm does not pass through any environment other than the necessary environment for cell survival or growth (e.g., normal atmosphere or atmosphere routinely used for cell culture (such as 95% air/5% $CO_2$), saline solution, or culture medium) between the illumination surface of the irradiation unit (see below) that configured to emit the light and the cell. In the case in which the cell to be irradiated is a cultured cell, the light in the wavelength range of 315-325 nm may pass through a culture vessel containing the cell (specifically, the lid, side wall, or bottom of the culture vessel) to irradiate the cells. In this case, it is preferable that the culture vessel is made of a material having a transmittance to the light in the wavelength range 315-325 nm of 40% or more, more specifically 50% or more, more specifically 60% or more, more specifically 70% or more, more specifically 75% or more, more specifically 80% or more, more specifically 85% or more, and more specifically 90% or more. Such materials may be, for example, glass, or plastic, more specifically, acrylic resin, polyethylene, polypropylene, polycarbonate, polystyrene, polyvinyl chloride, nylon, or the like.

The light in the range of 315-325 nm may be irradiated to the cell in one direction, or two, or three or more directions. In the case of two-direction irradiation, the two directions are preferably, but not limited to, opposite directions (e.g., upward and downward directions, leftward and rightward directions, or forward and backward directions).

In the case in which the cell to be irradiated is cultured in or on a substrate, such as agar medium, that has a low transmittance (of 50% for example) to the light in the wavelength range of 315-325 nm, the light is preferably irradiated to the cell from the above so as not to pass through the substrate.

The irradiation of the light in the range of 315-325 nm to the cell is preferably carried out within a closed space surrounded by a material adapted to block the light in the range of 315-325 nm (or having a transmittance of, for example, less than 5%, more preferably less than 1%, and more preferably 0.5% to the light in the wavelength range of 315-325 nm).

In the present disclosure, the cell to be irradiated is not particular limited and may be of any kind and in any developmental stage. Examples of cell include bacterial cells, yeast cells, plant cells or animal cells.

The cell may be a naturally-occurring cell (including a cancerous cell), an artificially-transformed cell (e.g., immortalized cell), an engineered cell, or a fused cell (also referred to as "hybridoma").

Preferably, the cell is a eukaryotic cell. The cells from a multicellular organism may be of one kind, or of a mixture of two or more kinds.

In some embodiments, the cell may be a yeast cell, a plant cell, or an animal cell. The animal, from which the cell originates, may be human, or any non-human animal. The non-human animals include companion animals, pet animals, zoo animals, industrial animals (e.g., farm animals), and wild animals. The non-human animals are, for example, vertebrates, which are preferably selected from mammals, birds and fish, more preferably mammals and birds, and more preferably mammals. Preferably, the animal cell is a human cell or a non-human animal cell.

In the case of an animal cell to be irradiated, it may be a totipotent, pluripotent, multipotent, progenitor or differentiated cell, or a mixture of any of the aforesaid cells. Examples of pluripotent cell include embryotic stem (ES) cells and induced pluripotent stem (iPS) cells. Examples of differentiated cell include skeletal muscle cells, smooth muscle cells, myocardial cells, nerve cells, fat cells, epithe-
lial cells, endothelial cells, immune cells, bone marrow cells,
and skin cells. In some particular embodiments, the cell may
be a skin cell. Skin cells include keratinocytes, fibroblasts,
melanocytes, and Langerhans cells. Some other particular
embodiments, the cell may be an excitatory cell. Excitatory
cells include nerve cells (or neurons), glial cells, muscle
cells (including myocardial cells, skeletal muscle cells and
smooth muscle cells), and endocrine cells.

In the case of an animal cell (especially a human cell), it
is preferable to irradiate the cell ex vivo or in vitro with the
light in the wavelength range of 315-325 nm.

The plant or animal cell may be a primary cultured cell,
or a subcultured cell, a cell from a tissue or organ culture
(e.g., a skin tissue culture). Cell culture may be adhesive or
non-adhesive culture (e.g., suspension or floating culture).

In embodiments wherein the cell to be irradiated is
cultured in an adhesive manner, the light in the wavelength
range of 315-325 nm is irradiated to the cells at a fluence that
does not cause cell detachment. In embodiments wherein the
cell is cultured in suspension, the light in the wavelength
range of 315-325 nm is irradiated to the cells at a fluence that
does not cause cell adhesion.

Cell culture conditions can be selected appropriately
according to the type of the cell used. The culture conditions
for animal cells may be: a temperature at or near about 36
to about 37° C., a relative moisture at or near about 90% to
about 95%, a $CO_2$ concentration at or near about 4% to about
10% (in particular, at or near about 5% to about 7%), an
almost neutral or alkaline pH (e.g., at or near about 7.0 to
7.7, more specifically at or near about 7.2 to 7.4). Culture
medium can be selected appropriately from known media
according to the type of the cell used. The culture medium
may be, for example, MEM, DMEM, F12, F10, M199,
DMEM/F12, RPMI 1640, BME or IMDM, or a combination
of any of the aforesaid media, or a modified medium thereof.
In the case in which the cell has potential to differentiate, the
culture medium may be a differentiation-induction medium.
The differentiation-induction medium can be selected appro-
priately from known media (e.g., E5™ medium, E6™
medium, E8™ medium, TeSR™ medium, TeSR™-E8™
medium) according to the type of the cell used and the type
of the differentiated cell of interest.

The culture medium may contain an additive(s) that is
commonly used in the art. The additives are known in the art
and include, for example, buffers (e.g., HEPES, DPBS,
HBSS, and bicarbonate buffer solution), amino acids (e.g.,
L-glutamine), vitamins, EDTA, antibiotics, serum, and
serum albumins. In the case in which the cell has potential
to differentiate, the additive may also include growth factors
and/or cytokines. Specific examples of growth factors and
cytokines include, for example, epidermal growth factor
(EGF), vascular endothelial growth factor (VEGF), fibro-
blast growth factor (FGF), nerve growth factor (NGF), stem
cell factor (SCF), activin A, bone induction factors (or bone
morphogenetic protein: BMP), interferons (INF), inter-
leukins, tumor necrosis factors (TNF), transforming growth
factors (TGF).

The cell irradiated with the light in the wavelength range
315-325 nm may be measured for a physiological event
involving calcium signaling. The measurement of the physi-
ological event involving calcium signaling can confirm the
induction of calcium channel and/or calcium pump expres-
sion in the cell. In the present disclosure, the term "mea-
surement" refers to detection or identification, or quantifi-
cation (including quantitative estimation) of a target to be
measured. The physiological events involving calcium signaling may be one or more selected from the group con-
sisting of, for example, muscle contraction (especially, an
amount of contraction and/or prolongation of muscle con-
traction), neuronal transmission (especially, an increase in
transmission efficiency (e.g., an increase in neurotransmitter
release)), mitochondrial activity (e.g., a degree of change in
membrane potential), cell death, glycogen degradation (es-
pecially accelerated degradation), cell differentiation (espe-
cially facilitated differentiation into osteoblast-like cells),
amino acid biosynthesis, carbon metabolism, antibiotic bio-
synthesis, and preferably from the group consisting of
muscle contraction, neuronal transmission, cell death, and
differentiation into osteoblast-like phenotype.

The cell having induced expression of a calcium channel
and/or a calcium pump by any of the above-mentioned
method according to the present disclosure can be used to
investigate and/or control a physiological event or phenom-
enon involving calcium signaling, for example, to control
muscle contraction, neuronal transmission, mitochondrial
activity, or cell death, accelerate glycogen degradation,
facilitate differentiation into osteoblast-like cells. Alterna-
tively, the cell can be used to search for an agent capable of
interacting the calcium channel and/or the calcium pump
(e.g., DHPR, VGCC, RYR, or SERCA).

An aspect of the present disclosure is a method of
modulating calcium signaling in a cell, the method com-
prising: inducing expression of a calcium channel and/or a
calcium pump in the cell by applying any of the method
described above to the cell; and measuring a physiological
event involving calcium signaling in the cell.

The physiological event can be measured by any of the
know techniques, which is selected appropriated according
to the event to be measured. For example, the physiological
event is one or more selected from the group consisting of
muscle contraction, neuronal transmission, cell death, and
osteoblast-like differentiation.

An aspect of the present disclosure is a method of making
a cell having induced expression of a calcium channel and/or
a calcium pump, comprising: irradiating a cell with light in
a wavelength range of 315-325 nm; and freezing the irra-
diated cell, wherein in the step of irradiating, the cell is not
irradiated with light at any wavelength of 200-300 nm, or is
irradiated with light in wavelengths of 200-300 nm at a
fluence that is less than 30% of that of the light in the
wavelength range of 315-325 nm, and is not irradiated with
light at any wavelength of 330-400 nm, or is irradiated with
light in wavelengths of 330-400 nm at a fluence that is less
than 50% of that of the light in the wavelength range of
315-325 nm.

The irradiation step is as described above for the method
of inducing expression of calcium channel and/or calcium
pump.

The method of freezing the irradiated cell is not particu-
larly limited and may be any of the known methods that can
be used for cell cryopreservation. For example, the cell may
be frozen by slow freezing, vitrification, or ultra-rapid
vitrification.

For example, the cell may be frozen in suspension in a
suitable culture medium (e.g., any medium described above)
in a suitable vessel. The vessel may be, for example, a tube,
vial, well plate, or cell freezing vessel (e.g., BICELL bio
freezing vessel (NIHON FREEZER CO., LTD.), CoolCell®
(Corning Inc.), or Mr. Frosty™ (Thermo Fisher Scientific
Inc.)). The culture medium may be supplemented with a
cryoprotectant. Any of the known cryoprotectants may be
used, that can be used for cell cryopreservation, including
dimethyl sulfoxide (DMSO), glycerol, polyethylene glycol, propylene glycol, sucrose, glycerin, polyvinylpyrrolidone, sorbitol, dextran, trehalose, hydroxyl ethyl starch, and the like. The concentration added may usually be 2-10% (w/v or v/v).

The frozen cell may be stored in, for example, a deep freezer, at a temperature of, for example, −50° C. or lower, or in liquid nitrogen at a temperature of, for example, −180° C. or lower.

The cell subjected to the step of irradiating has induced expression of calcium channel and/or calcium pump, as described above, and thus the expression is increased in the cell. By freezing, the cell can retain increased expression of calcium channel and/or calcium pump until after thawing. Therefore, the frozen cell can be easily used after thawing, for example, as an evaluation system for an effect on calcium channel and/or calcium pump and/or calcium flow.

<Cell Culture Apparatus>

Another aspect of the present disclosure provides an apparatus for culturing a cell. The apparatus according to one embodiment of the present disclosure includes: a (first) irradiation unit configured to mainly emit light in a wavelength range of 315-325 nm; a (first) mounting unit configured to support a cell culture vessel and located within an irradiation area of the (first) irradiation unit; a (first) irradiation control unit configured to control the (first) irradiation unit; and a housing configured to accommodate the (first) irradiation unit and the (first) mounting unit therein.

The apparatus according to the present disclosure is suitable to carry out an above-described method of inducing expression of a calcium channel and/or a calcium pump in a cell, according to the present disclosure. The cell irradiated with the light in the wavelength range of 315-325 nm by using the cell culture apparatus according to the present disclosure has induced expression of calcium channel and/or calcium pump, as described above, and therefore may be subsequently cultured for investigating or controlling a physiological event involving calcium signaling.

The cell that is suitable for culture by using the cell culture apparatus according to the present disclosure is as described above in the section "<Method of inducing expression of a calcium channel and/or a calcium pump>."

The apparatus according to the present disclosure includes in a housing, at least one irradiation unit configured to mainly emit light in a wavelength range of 315-325 nm. Preferably, the irradiation unit is configured to substantially exclusively emit the light in the wavelength range of 315-325 nm.

In the present specification, the phrase light source configured to "mainly emit light in a wavelength range of 315-325 nm" or "be configured to mainly emit light in a wavelength range of 315-325 nm" refers to a light source configured to emit or be configured to emit the light in the wavelength range of 315-325 nm at an irradiance that is 50% or more of, more particularly 60% or more of, more particularly 70% or more of, more particularly 80% or more of, and more particularly 90% or more of, the total irradiance of the light emitted by the light source (i.e., the irradiance of the light in the entire wavelength range). In the present specification, the phrase light source configured to "substantially exclusively emit light in a wavelength range of 315-325 nm" or "be configured to substantially exclusively emit light in a wavelength range of 315-325 nm" refers to a light source configured to emit or be configured to emit the light in the wavelength range of 315-325 nm at an irradiance that is 95% or more of, more particularly 98% or more of, and more particularly 99% or more of, the total irradiance of the light emitted by the light source.

The irradiation unit includes at least one light source configured to emit light in a wavelength range of 315-325 nm. Examples of the light source include light-emitting diodes (LEDs) and laser diodes (LDs), as well as xenon lamps, metal halide lamps, and high-pressure mercury lamps, which have a necessary optical filter. In the case in which the light emitted by the light source used has a relatively low ratio in radiant intensity of the light in the wavelength range of 315-325 nm with respect to the light in the entire wavelength range (of, for example, less than 30%, more particularly 40%, and more particularly 50%), a filter may be used to increase the ratio, which filter has a transmittance to the light in the wavelength range of 315-325 nm higher than that of light outside the said wavelength range.

In view of energy efficiency, the light source configured to emit the light in the wavelength of 315-325 nm preferably is a light source configured to mainly emit the light in the wavelength range of 315-325 nm, and more preferably a light source configured to substantially exclusively emit the light in the wavelength range of 315-325 nm.

The light source configured to mainly or substantially exclusively emit the light in the wavelength range of 315-325 nm may be a light source configured to emit light having the main peak wavelength in the wavelength of 315-325 nm, preferably 316-324 nm, more preferably 317-323 nm, and more preferably 318-322 nm. More specifically, the light source may be a light source configured to light having a wavelength spectrum with a peak wavelength (especially a single peak) at 320±5 nm (preferably 320±3 nm) and a full width at half maximum in a range of 1-20 nm (preferably 1-10 nm, and more preferably 1-5 nm). Examples of such light sources include light-emitting diodes (LEDs) and laser diodes (LDs). The light source may be a cluster or an array of LEDs or LDs. In view of energy efficiency and economic efficiency, use of LED or LD is preferable due to the energy intensiveness, low heat generation, low power consumption and long life. In addition, the irradiance (fluence rate) or the fluence can be easily controlled.

The irradiation unit may include a light diffusion member and/or a light reflective member in the pathway of light emitted from the light source. The light diffusion member is not particularly limited and may be any of the known light diffusion members. Specific examples of light diffusion members include frosted, opal and holographic diffuser members. The light reflective member is not particularly limited and may be any of the known light reflective members. Specific examples of light reflective members include mirrors and prisms. In some particular embodiments, the irradiation unit includes a surface light emitter composed of a light source (e.g., LD or LED), a light guide member, and a light diffusion member and/or a light reflective member Preferably the irradiation unit is configured to be configured to irradiate the light in the wavelength range of 315-325 nm to the cell at a generally uniform irradiance.

The irradiation unit may be configured to be configured to (e.g., mainly or substantially exclusively) emit light in a specified wavelength range outside the wavelength range of 315-325 nm. In other words, the irradiation unit may include a light source to (preferably mainly and more preferably substantially exclusively) emit the light in the wavelength range of 315-325 nm as well as another light source(s) to (e.g., mainly or substantially exclusively) emit the light in the specified wavelength range. Alternatively, the irradiation unit may include an optical filter to transmit the light in the wavelength range of 315-325 nm, and an optical filter to transmit the light in the specified wavelength range so that the irradiation unit can (preferably mainly and more preferably substantially exclusively) emit light in a desired wavelength region by switching the filters.

The light in the specified wavelength range may be, for example, light in a range of 100-290 nm, more particularly 190-290 nm, more particularly 200-280 nm, more particularly 240-280 nm or 210-220 nm. The light in such a wavelength range can be used to disinfect or sterilize the mounting unit and/or the atmosphere around the mounting unit (i.e., as disinfecting or sterilizing light) before and/or after cell culture. As a light source to emit the light, any of the known germicidal or sterilizing lamps can be used, including LEDs and LDs.

Another example of the light in the specified wavelength range may be white light. White light can be used for illumination at operation and/or observation. White light sources include fluorescent lights, incandescent lights, and white LEDs, with white LEDs being preferable.

The irradiation unit may be arranged to irradiate the mounting unit in at least one direction of a downward direction (from the overhead of mounting unit, for example), an upward direction (from beneath mounting unit, for example) and a lateral direction (from right beside mounting unit, for example).

In some embodiments, the irradiation unit is arranged above the mounting unit (therefore above a cell culture vessel placed on the mounting unit). This arrangement makes it possible to avoid the attenuation of the light in the wavelength range of 315-325 nm irradiated from the irradiation unit by passing through an ultraviolet light absorbing substrate, such as agar medium, thus allowing to easily control the fluence or irradiance of the light in the wavelength range of 315-325 nm.

The cell culture apparatus according to the present disclosure includes an irradiation control unit configured to control the irradiation unit. In the case in which the cell culture apparatus according to the present disclosure includes a plurality of irradiation units, different irradiation control units may control the different irradiation units, or a single irradiation control unit may control two or more irradiation units or all the irradiation units included in the apparatus.

The irradiation control unit may control the irradiation unit to emit continuous light or intermittent light, or a combination thereof. Intermittent light can avoid or reduce a rise in temperature of the cell and/or the irradiation unit (especially, the light source).

The irradiation control unit may control the irradiation unit to emit pulsed light, for example, having a pulse width of 100 ms or less, more specifically 50 ms or less, more specifically 20 ms or less, more specifically 10 ms or less, and more specifically 5 ms or less, and a duty ratio of 50% or less, more specifically 40% or less, more specifically 30% or less, more specifically 20% or less, more specifically 10% or less, and more particularly 5% or less.

The irradiation control unit may also control the irradiation unit to emit the light in the wavelength range of 315-325 nm at an irradiant that is in a predefined range on the mounting surface of the mounting unit.

The predefined irradiance range can be determined appropriately according to the cell used and/or the desired degree of the effect (induction of expression of calcium channel and/or calcium pump) and may be, for example, a range of 0.1-300 mW/cm$^2$, more particularly a range of 0.5-200 mW/cm$^2$, more particularly 1-100 mW/cm$^2$, more particularly 5-50 mW/cm$^2$, and more particularly 5-20 mW/cm$^2$. Controlling the irradiance of the light from the irradiation unit (or radiant intensity of the light emitted from the irradiation unit) within the said range can provide irradiance or fluence effective in achieving the desired effect in the cell in a cell culture vessel placed on the mounting unit.

An irradiance of less than 0.1 mW/cm$^2$ or more than 300 mW/cm$^2$ may not efficiently achieve the desired effect.

For these purposes, the irradiation control unit may be, for example, a pulse width modulation circuit.

The irradiation control unit may also control the irradiation unit to emit the light in the wavelength range of 315-325 nm during a predefined period of irradiation time.

The lower limit of the irradiation time may be, for example, 1 second, 2 seconds, 5 seconds, 10 seconds, 20 seconds, 30 seconds, 1 minute, 2 minutes, or 5 minutes. The upper limit may be, for example, 5 hours, 2 hours, 1 hour, 30 minutes, 15 minutes, or 10 minutes. A particular irradiation time may be in a range of between a lower limit value and an upper limit value, where the lower limit value is selected from the above-mentioned lower limit values and the upper limit value is selected from the above-mentioned upper limit values. Specific examples of the irradiation time include, but not limited to, 5 seconds to 5 hours, more specifically 5 seconds to 2 hours, more specifically 5 seconds to 1 hour, more specifically 5 seconds to 30 minutes, more specifically 10 seconds to 30 minutes, more specifically 10 seconds to 15 minutes.

For these purposes, the irradiation control unit may be, for example, a timer.

In certain specific embodiments, the irradiation control unit controls the irradiant on the mounting surface of the mounting unit and the irradiation time (or the fluence on the mounting surface) of the light in the wavelength range of 315-325 nm emitted from the irradiation unit. In the embodiments, the irradiation control unit may be, for example, a pulse width modulation circuit and a timer.

In more specific embodiments, the irradiation control unit may control the irradiation unit to emit the light in the wavelength range of 315-325 nm at an fluence within a range of, for example, 10-5000 mJ/cm$^2$, in particular 50-4500 mJ/cm$^2$, 100-4000 mJ/cm$^2$, 200-3500 mJ/cm$^2$, 300-3000 mJ/cm$^2$, 400-2500 mJ/cm$^2$, 500-2000 mJ/cm$^2$, and 500-1500 mJ/cm$^2$.

The irradiation control unit may control the irradiation unit according to the signal received from a sensor that is provided within the irradiation area of the irradiation unit on the level of the mounting surface.

In the embodiments in which the irradiation unit is also configured to emit light in a specified wavelength range outside the wavelength range of 315-325 nm (e.g., sterilizing light or white light), the irradiation control unit may control the irradiation unit to emit the light in the specified wavelength range in certain cases or not to emit the light in other certain cases.

For example, in the embodiments in which the irradiation unit is also configured to emit disinfecting or sterilizing light, the irradiation control unit may control the irradiation unit to emit the disinfecting or sterilizing light only when a door (especially an inner door) of the housing is closed. Alternatively or additionally, the irradiation control unit may control the irradiation unit in order not to emit the disinfecting or sterilizing light simultaneously with the light in the wavelength range of 315-325 nm.

The cell culture apparatus according to the present disclosure includes, in the housing, at least one mounting unit configured to support a cell culture vessel.

Two or more mounting units may be provided at different locations from each other horizontally and/or vertically (preferably, perpendicularly).

The mounting unit is located within the irradiation area of the irradiation unit. Therefore, when a culture vessel containing a cell(s) is placed on the mounting unit, the light in the wavelength range of 315-325 nm emitted from the irradiation unit can be irradiated to the cell(s). In the embodiments in which two or more mounting units are provided, the two or more mounting units may be located within the irradiation area of one irradiation unit, or within the irradiation areas of two or more irradiation units. Different mounting units may be located within the respective irradiation areas of different irradiation units.

The mounting unit is not particularly limited so long as it has a structure that allows mounting and a size sufficient to allow mounting a culture vessel used on the top surface. The mounting unit may be designed according to the culture vessel used. The culture vessel that can be used with the cell culture apparatus according to the present disclosure may be any of the known vessels used for cell culture, including petri dishes, dishes, beakers, flasks, bottles, micro well plate, and the like.

The mounting unit may be composed of, for example, at least a portion of the top surface of a shelf, rack, shelf netting, table, platform or pedestal, or the inner bottom surface of the housing. The mounting surface is not limited to a continuous surface, and may be composed of a plurality of discrete surfaces, or may be an imaginary surface such as the top surface of a mesh or grid shelf. The mounting unit may be made of, for example, metal (such as iron, stainless steel, aluminum or brass), glass or plastic (such as acrylic resin, polycarbonate resin or polyvinyl chloride resin).

In some embodiments, the mounting unit is made of a material opaque to the light in the wavelength range of 315-325 nm. Especially in the case in which the light in the wavelength range of 315-325 nm is irradiated from above, the embodiments makes it possible to avoid the irradiation of the light passing through the (first) mounting unit to (a cell(s) in a culture vessel mounted on) the (second) mounting unit, which may be provided below the (first) mounting unit, thus allowing to easily and separately control the fluence or irradiance of the light in the wavelength range of 315-325 nm on the respective mounting units.

The mounting unit may have a recess or a protrusion defining an area (mounting surface) where a culture vessel is mounted or placed. In the case in which the mounting unit has a recess, the vessel may be mounted or placed on the bottom of the recess. In the case in which the mounting unit has a protrusion or plural protrusions, the vessel may be mounted or placed on the top surface of the protrusion or in the area defined by the protrusions.

One mounting unit may be configured to support a single culture vessel, or two or more culture vessels.

The cell culture apparatus according to the present disclosure includes a housing configured to accommodate at least the mounting unit and the irradiation unit therein. The irradiation control unit may be provided out of the housing, or built into the housing.

The housing may have an opening on one surface (preferably a side surface) and may further have a door to open and close the opening. The door may be composed of an inner door and an outer door. At least a portion of the inner door may be made of a material, such as glass containing an inorganic UV absorber, or a member, such as glass or plastic plate with a film of an organic UV absorber, having a transmittance of 50% or more, preferably 60% or more, more preferably 70% or more, more preferably 80% or more, more preferably 90% or more, and more preferably 95% or more, to visible light and a transmittance of 20% or less, preferably 10% or less, more preferably 5% or less, and more preferably 1% or less, to the light in a wavelength range of 315-325 nm, so as to observe the cell culture compartment(s) inside the housing.

The shape of the housing may be, for example, cubic, rectangular or the like. The housing is preferably made of a material opaque to the light in a wavelength range of 315-325 nm, for example, metal (such as iron, stainless steel, aluminum, or brass). The interior space of the housing may be surrounded by heat insulator.

In the embodiments in which the mounting unit is a portion of a shelf, rack, shelf netting, or table, a support member for the shelf, rack, shelf netting, or table is provided inside the housing.

The inner space of the housing may be divided vertically (or perpendicularly) and/or horizontally into two or more compartments (herein also referred to as "cell culture compartments"). The two or more cell culture compartments may be formed by vertically dividing the inner space of the housing by, for example, one or more shelves, racks, shelf netting, or tables. Additionally or alternatively, the two or more cell culture compartments may be formed by horizontally dividing the inner space of the housing by, for example, one or more side walls.

The two or more cell culture compartments are preferably configured to be in fluid communication with one another such that the atmosphere can circulate through the compartments via for example, a plurality of openings of the shelves or tables (especially outside the irradiated area) or interspaces between the shelves or tables and one or two inner side walls of the housing (e.g., front and/or rear side walls), or another communication mechanism (e.g., duct).

In the embodiments in which the inner space of the housing is divided into two or more cell culture compartments, the apparatus of the present disclosure may include a light blocking member to block light in a wavelength range of 315-325 nm (with a transmittance of, for example, less than 5%, more preferably less than 1%, and more preferably less than 0.5% to the light in the wavelength range 315-325 nm). The light blocking member is located in the housing to prevent the light in the wavelength range of 315-325 nm emitted from the (first) irradiation unit provided in a certain cell culture compartment (e.g., an upper compartment) from being irradiated to the (second) mounting unit provided in another cell culture compartment (e.g., a lower compartment).

In the embodiments, a set of irradiation unit and mounting unit is provided in each cell culture compartment, in which the mounting unit is located outside the irradiation areas of the irradiation units located in the other compartments. The embodiments make it possible to culture cells in a plurality of cell culture vessels under irradiation of the light in the wavelength range of 315-325 nm at an irradiance, which is controlled for each vessel or for each set of vessels.

Therefore, in some preferable embodiments, the cell culture apparatus according to the present disclosure includes in the housing: a second irradiation unit configured to mainly emit light in a wavelength range of 315-325 nm and located below the first mounting unit; a second mounting unit configured to support a cell culture vessel and located within an irradiation area of the second irradiation unit; and a light blocking member configured to block light in a wavelength range of 315-325 nm and located to prevent the light in the wavelength range of 315-325 nm emitted from the first irradiation unit, from being irradiated to the second mounting unit (thereby locating the second mounting unit outside the irradiation area of the first irradiation unit).

The apparatus further includes a second irradiation control unit configured to control the second irradiation unit.

The apparatus according to the embodiments may include in the housing, two or more light blocking members as needed, and therefore can include three or more sets of irradiation units and mounting units. The first irradiation control unit may also serve as the second light control unit. The mounting unit is provided on the top surface of the light blocking member. In other words, the top surface of the light blocking member may also serve as the mounting unit.

The light blocking member is made of, for example, metal, such as iron, stainless steel, aluminum, brass or the like.

The cell culture apparatus according to one embodiment of the present disclosure may further includes a thermal controller unit configured to heat and maintain the atmosphere in the housing and/or the cell culture vessel placed on the mounting unit at a predefined temperature. The embodiment can maintain the temperature of the cell cultured in the cell culture vessel at a suitable temperature, thereby reducing the influence of temperature changes before, during and/or after the irradiation on the viability of the cell.

The thermal controller unit may be configured to heat to a predefined temperature or a predefined temperature range of about 36° C. to about 37° C. The thermal controller unit may be composed of, for example, a heating body (such as heater, Peltier element, or the like) and/or a heat transfer medium (such as water, oil, metal, or the like), and a temperature controlling member to control the temperature of the heating body and/or the heat transfer medium. The thermal controller unit may include a thermal sensor configured to sense the temperature of the atmosphere in the housing and/or the cell culture vessel placed on the mounting unit.

The cell culture apparatus according to one embodiment of the present disclosure may further includes a humidity controller unit configured to humidify and maintain the atmosphere in the housing at a predefined humidity or humidity range.

The humidity controller unit may be configured to feed moisture to a predefined humidity or humidity range of about 90% to about 95%. The humidity controller unit may be composed of, for example, a natural evaporative humidifier, or may be composed of a humidity sensor to sense the humidity of the atmosphere in the housing, a steam feeder, and a humidity controlling member configured to control the steam feeder according to the signal received from the humidity sensor.

The cell culture apparatus according to one embodiment of the present disclosure may further includes a $CO_2$ concentration controller unit configured to feed $CO_2$ gas and maintain the $CO_2$ concentration of the atmosphere in the housing to a predefined concentration or concentration range.

The $CO_2$ concentration controller unit may be configured to feed $CO_2$ gas at a predefined concentration or concentration range of about 5% to about 7%. The $CO_2$ concentration controller unit may be composed of, for example, a $CO_2$ concentration sensor to sense the $CO_2$ concentration of the atmosphere in the housing, a $CO_2$ feeder, and a $CO_2$ concentration controlling member configured to control the $CO_2$ feeder according to the signal received from the $CO_2$ concentration sensor.

The cell culture apparatus according to one embodiment of the present disclosure may further includes a display unit. The display unit configured to be configured to display information on the light in the wavelength range of 315-325 nm (for example, the irradiance on the mounting unit and/or the irradiation time and/or the fluence). In this embodiment, the display unit may display the information based on the signal received from the irradiation control unit or on the signal(s) received from the sensor(s) included in the thermal controller unit and/or the humidity controller unit and/or the $CO_2$ concentration controller unit.

Alternatively or additionally, the display unit may display the temperature and/or the humidity and/or the $CO_2$ concentration of the atmosphere in the housing of the cell culture apparatus according to the present disclosure. In this embodiment, the display unit may display the information based on the signal(s) received from the sensor(s) included in the thermal controller unit and/or the humidity controller unit and/or the $CO_2$ concentration controller unit.

The display unit may be composed of a display and a display controlling member configured to control the display.

The cell culture apparatus according to one embodiment of the present disclosure may further includes a mechanism, such as fan, configured to agitate and/or circulate the atmosphere in the housing.

In the cell culture apparatus according to the present disclosure, it is preferable not to arrange any member, the transmittance of which is substantially changed by irradiation of the light in the wavelength range of 315-325 nm, excluding the optical members constituting the irradiation unit, on the optical path of the light from the irradiation unit to the mounting unit (especially, the cell to be irradiated on the mounting unit). This preferable embodiment makes it possible to easily control the fluence or irradiance of the light in the wavelength range of 315-325 nm irradiated to the cell in the cell culture vessel placed on the mounting unit.

The apparatus according to the present disclosure is hereinafter described with reference to FIGS. 1 to 3, which schematically illustrate specific embodiments of the cell culture apparatus of the present disclosure.

Embodiment 1

In some embodiments of the present disclosure, the cell culture apparatus 100 includes: an irradiation unit 112, which is configured to mainly emit light in a wavelength range of 315-325 nm; a mounting unit 114, which is configured to be located within the irradiation area of the irradiation unit 112 and support a cell culture vessel 150; an irradiation control unit 110, which is configured to control the irradiation unit 112; and a housing 118, which is configured to accommodate the irradiation unit 112 and the mounting unit 114, as illustrated in FIG. 1.

The cell culture apparatus 100 may include, as an optional component, an optical sensor 120 within the irradiation area of the irradiation unit 112.

In FIG. 1, the irradiation unit 112 is provided on the inner top surface of the housing 118. However, this exemplary arrangement is non-limiting. The irradiation unit 112 may be provided on the upper part(s) of one or more of the side walls (e.g., the rear side wall and/or the right and left side walls) or on another structure (e.g., shelf plate or rack) provided above the mounting unit.

In FIG. 1, the mounting unit 114 is formed as a part of a shelf plate 140 or a rack. However, the mounting unit 114 may be defined as a portion of the inner bottom surface of the housing, or a platform provided on the inner bottom surface.

In FIG. 1, the irradiation control unit 110 is located outside the housing 118 on or above its top surface. However, the mounting unit 110 may be located on a side (any of the front, back, right and left sides) of, or underneath the housing.

The irradiation unit 112 can irradiate light in a wavelength range of 315-325 nm to a cell(s) cultured in a cell culture vessel 150 (e.g., Petri dish), which is mounted on the mounting unit 114.

The optical sensor 120, if provided, is configured to sense the light in the wavelength range of 315-325 nm at the level of the mounting surface. The expression "the level of the mounting surface" means any locations in the mounting surface as well as any locations that are outside the mounting surface but can be regard as equivalent to the mounting surface for the sensing. The optical sensor 120 is configured to transmit to the irradiation control unit 110, a signal according to the sensed amount of the light in the wavelength range of 315-325 nm. Based on the signal received, the irradiation control unit 110 is configured to control the irradiation unit 112 to emit the light in the wavelength range of 315-325 nm at an appropriate radiant intensity to provide a desired irradiance at the level of the mounting surface.

Embodiment 2

Figure 2:
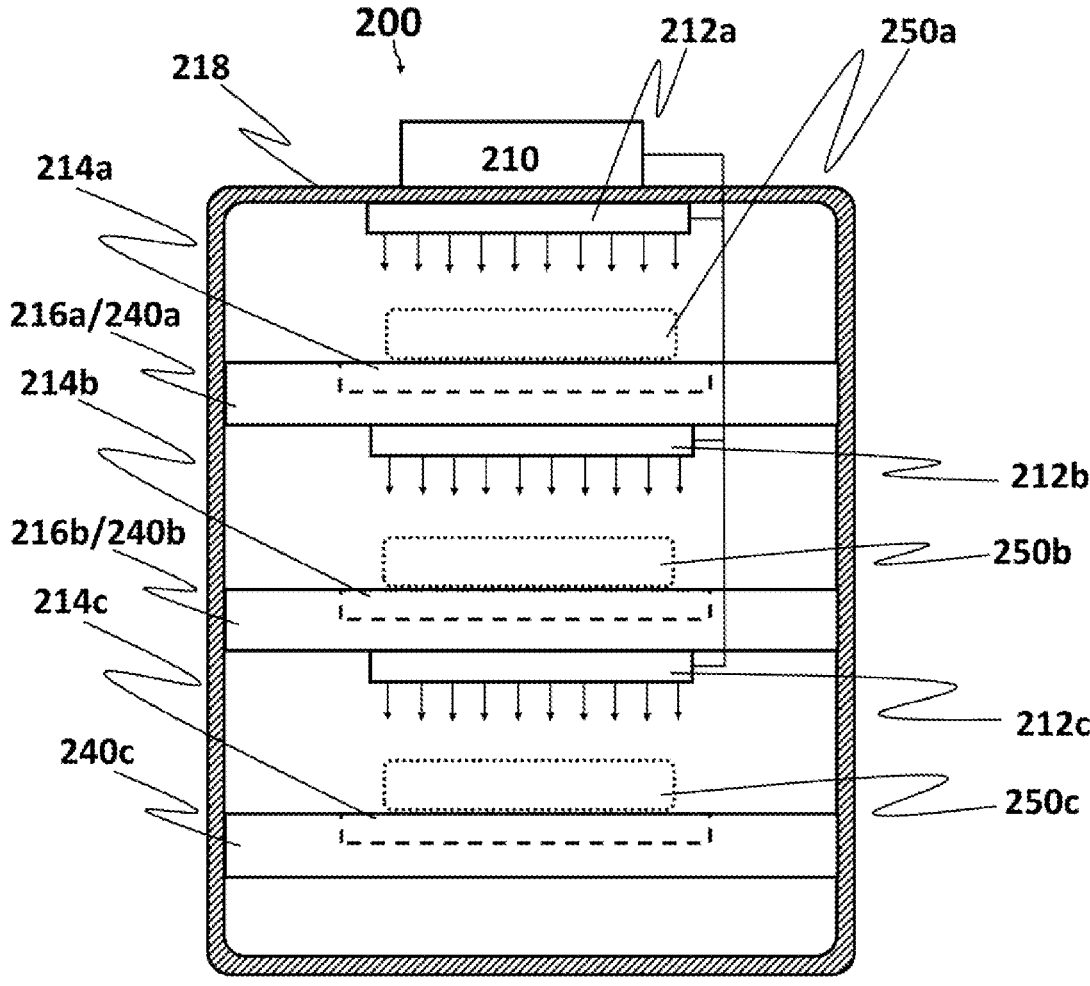
FIG. 2 illustrates Embodiment 2 of an apparatus according to the present disclosure.

In some embodiments of the present disclosure, the cell culture apparatus 200 includes: a first irradiation unit 212a, which is configured to mainly emit light in a wavelength range of 315-325 nm; a first mounting unit 214a, which is configured to be located within the irradiation area of the first irradiation unit 212a and support a cell culture vessel 250a; a second irradiation unit 212b, which is configured to be mainly emit light in a wavelength range of 315-325 nm; a second mounting unit 214b, which is configured to be located within the irradiation area of the second irradiation unit 212b and support a cell culture vessel 250b; an irradiation control unit 210, which is configured to control the first and second irradiation units 212a, 212b; a first light blocking member 216a, which is configured to block light in a wavelength range of 315-325 nm; and a housing 218, which is configured to accommodate therein, the irradiation units 212a, 212b, the mounting units 214a, 214b, and the first light blocking member 216a, as illustrated in FIG. 2.

In the housing 218, the second irradiation unit 212b is located below the first mounting unit 214a, and the first light blocking member 216a is located to prevent the light in the wavelength range of 315-325 nm from the first irradiation unit 212a, from being irradiated to (the cell(s) in the cell culture apparatus 250 placed on) the second mounting unit 214b. In other words, the second mounting unit 214b is located outside the irradiation area of the first irradiation unit 212a, which is located above the second irradiation unit 212b.

The cell culture apparatus 200 may include in the housing 218, the following optional components: a third irradiation unit 212c, which is configured to be mainly emit light in a wavelength range of 315-325 nm and be controlled by the irradiation control unit 210; a third mounting unit 214c, which is configured to be located within the irradiation area of the third irradiation unit 212c and support a cell culture vessel 250c; and a second light blocking member 216b, which is configured to block light in a wavelength range of 315-325 nm. In the housing 218, the third irradiation unit 212c is located below the second mounting unit 214b, and the second light blocking member 216b is located to prevent the light in the wavelength range of 315-325 nm from the first irradiation unit 212a and the light in the wavelength range of 315-325 nm from the second irradiation unit 212b from being irradiated to the third mounting unit 214c.

In FIG. 2, the inner space of the housing 218 is divided into three cell culture compartments. However, the inner space may be divided into two cell culture compartments or into four or more cell culture compartments.

In the cell culture apparatus 200, in which cell culture vessels 250a, 250b, 250c are placed on the mounting units 214a, 214b, 214c, respectively, each containing a cell(s), the first irradiation unit 212a can irradiate light in a wavelength range of 315-325 nm to only the cell(s) in the cell culture vessel 250a, the second irradiation unit 212b can irradiate light in a wavelength range of 315-325 nm to only the cell(s) in the cell culture vessel 250b, and the third irradiation unit 212c can irradiate light in a wavelength range of 315-325 nm to only the cell(s) in the cell culture vessel 250c.

In FIG. 2, the three irradiation units 212a, 212b, 212c are controlled by a single irradiation control unit 210. However, they may be controlled by the respective three irradiation control units.

Figure 3A:
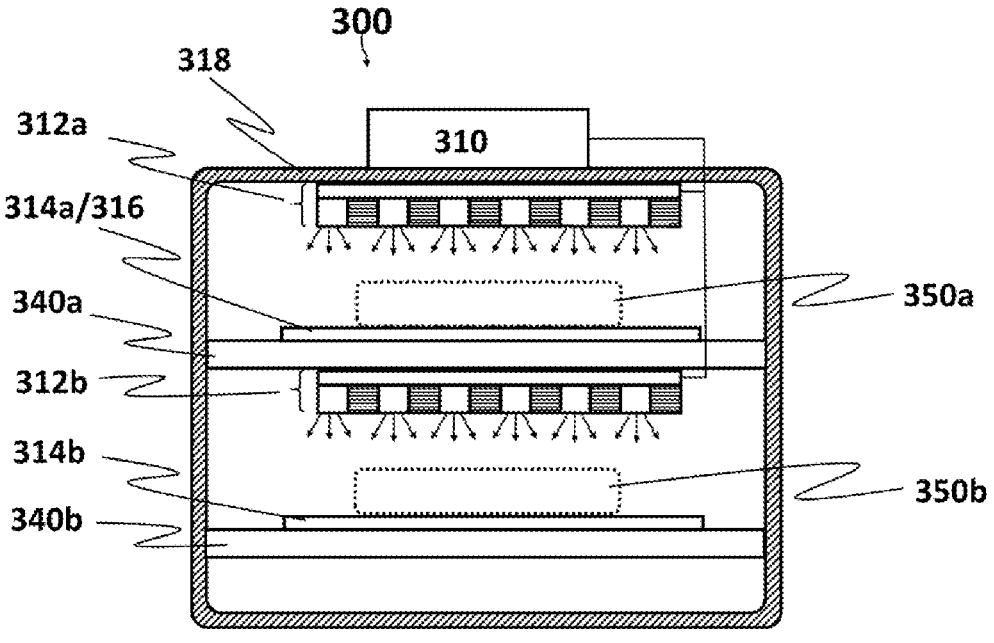
FIGS. 3A and 3B illustrate Embodiment 3 of an apparatus according to the present disclosure.
Figure 3B:
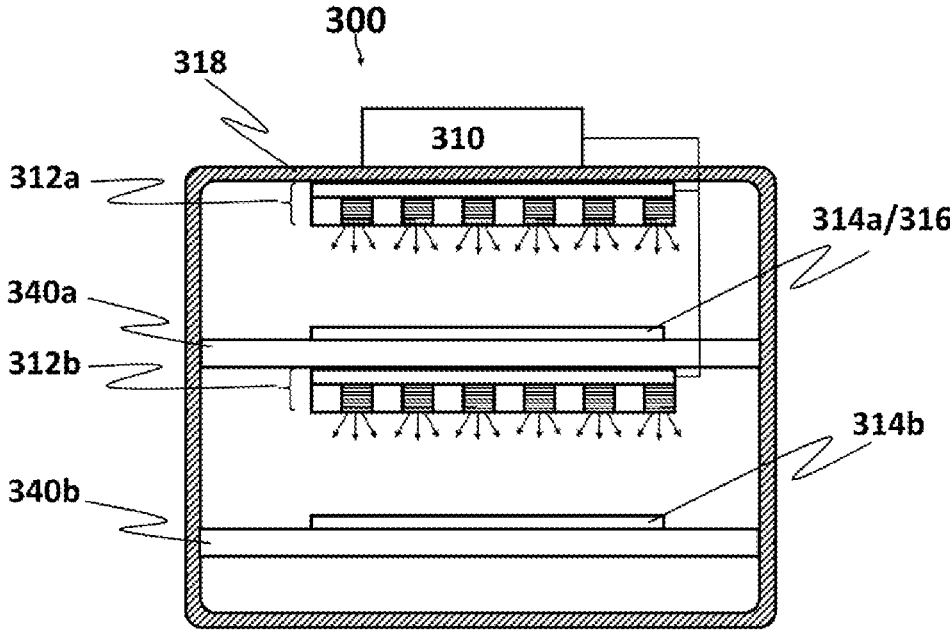

In FIG. 2, the mounting units 214a, 214b, 214c are formed as respective parts of the shelf plates 240a, 240b, 240c. However, they may be each as another structure provided on the respective shelf plates or racks, as illustrated in FIGS. 3A and 3B.

In FIG. 2, the whole of each of the shelf plates 240a, 240b also serves as a light blocking member 216a, 216b. A portion of each of the shelf plates 240a, 240b may serve as a light blocking member 216a, 216b so long as it can prevent the light in the wavelength range of 315-325 nm emitted from the irradiation unit 212a (for light blocking member 216a) or the irradiation units 212a, 212b (for light blocking member 216b), which are located in the upper cell culture compartment, from being irradiated to the mounting unit 214b, 214c in the lower cell culture compartment. The light blocking member 316 may be as a different structure from the shelf plate 340a, as illustrated in FIGS. 3A and 3B.

In FIG. 2, a humidifier and/or a flow generating mechanism (such as a fan) are provided the compartment underneath the third mounting unit 214c. In this embodiment, the shelf plates 240a, 240b, 240c are not in contact with the front and/or rear side wall of the housing (in the view of FIG. 2), or each have an opening(s) outside the irradiation area of the irradiation unit 212a, 212b, 212c. The embodiment makes it possible to maintain in the cell culture compartments, a homogeneous atmosphere under the desired culture conditions.

The remaining features of this embodiment are as described for Embodiment 1.

Embodiment 3

In some embodiments of the present disclosure, the cell culture apparatus 300 includes: a first irradiation unit 312a, which is configured to mainly emit light in a wavelength range of 315-325 nm; a first mounting unit 314a, which is configured to be located within the irradiation area of the first irradiation unit 312a and support a cell culture vessel 350a; a second irradiation unit 312b, which is configured to be mainly emit light in a wavelength range of 315-325 nm; a second mounting unit 314b, which is configured to be located within the irradiation area of the second irradiation unit 312b and support a cell culture vessel 350b; an irradiation control unit 310, which is configured to control the first and second irradiation units 312a, 312b; a light blocking member 316a, which is configured to block light in a wavelength range of 315-325 nm; and a housing 318, which is configured to accommodate therein, the irradiation units 312a, 312b, the mounting units 314a, 314b, and the light blocking member 316, as illustrated in FIGS. 3A and 3B.

In this embodiment, the mounting units 314a, 314b, are each a plate provided on the mesh plates 340a, 340b, respectively. The mounting unit 314a also serves as the light blocking member 316.

In the housing 318, the second irradiation unit 312b is located below the first mounting unit 314a, and the light blocking member 316 is located to prevent the light in the wavelength range of 315-325 nm from the first irradiation unit 312a, from being irradiated to (the cell(s) in the cell culture apparatus 350b placed on) the second mounting unit 314b. In other words, the second mounting unit 314b is located outside the irradiation area of the first irradiation unit 312a, which is located above the second irradiation unit 312b.

The irradiation units 312a, 312b are also configured to mainly emit light in a specified wavelength range outside the wavelength range of 315-325 nm (disinfecting ultraviolet light or white light) and configured to switch among the turn-off state, the state in which the irradiation unit mainly emits the light in the wavelength range of 315-325 nm, and the state in which the irradiation unit mainly emits the light in the specified wavelength range.

As shown in FIG. 3A, in the cell culture apparatus 300, in which cell culture vessels 350a, 350b are placed on the mounting units 314a, 314b, respectively, each containing a cell(s), the first irradiation unit 312a can irradiate light in a wavelength range of 315-325 nm to the cell(s) in the cell culture vessel 350a, and the second irradiation unit 312b can irradiate light in a wavelength range of 315-325 nm to the cell(s) in the cell culture vessel 50b.

FIG. 3B illustrates an embodiment in which the light in the specified wavelength range is a disinfectant ultraviolet light. Before and/or after cell culture in the cell culture apparatus 300, the irradiation units 312a, 312b can be used to irradiate the disinfecting ultraviolet light (e.g., light in a wavelength range of 200-280 nm, in particular in a wavelength range of 240-280 nm or 210-220 nm) to the cell culture compartments so as to disinfect them. The irradiation control unit 310 can control the irradiation units 312a, 312b so as not to simultaneously emit the light in the wavelength of 315-325 nm and the disinfecting ultraviolet light. Additionally or alternatively, the irradiation control unit 310 may control the irradiation units 312a, 312b so that they can emit the disinfecting ultraviolet light only when a door (especially an inner door), which is provided in the housing 318, is closed.

The irradiation units 312a, 312b may also be configured to emit white light as another light in a specified wavelength range outside the wavelength range of 315-325 nm. In this configuration, white light can be used to illuminate the cell culture compartments of the cell culture apparatus 300 in order to facilitate easy operation and/or observation. In configuration where the irradiation units 312a, 312b are configured to emit the disinfecting ultraviolet light and white light, the irradiation control unit 310 can control the irradiation units 312a, 312b so as not to simultaneously emit the disinfecting ultraviolet light and white light.

The remaining features of this embodiment are as described for Embodiments 1 and/or 2.

EXPERIMENTS

Figure 4:
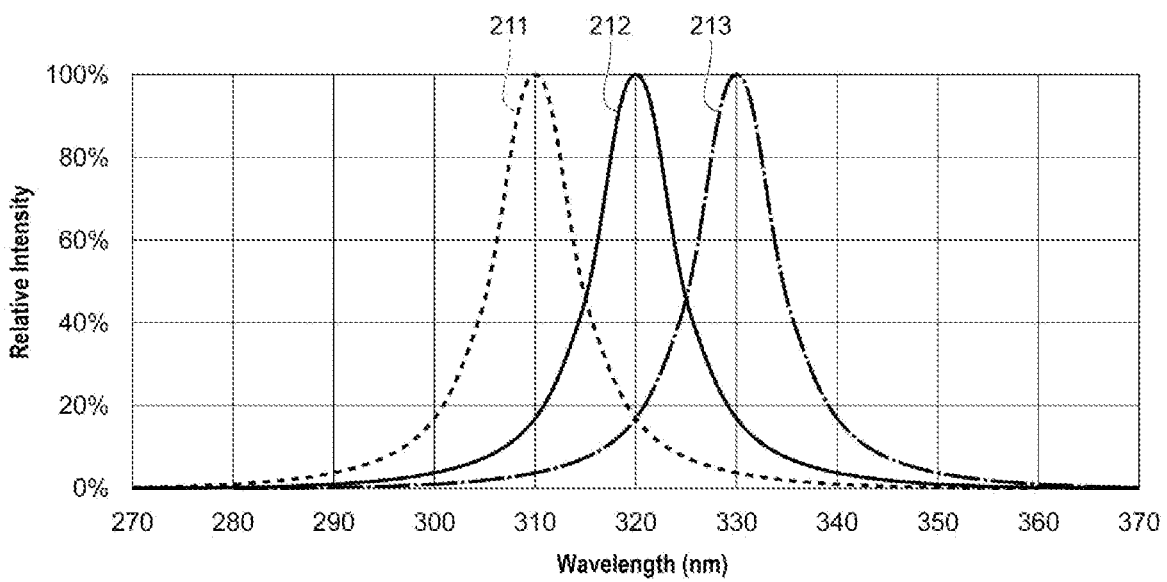
FIG. 4 shows the emission spectra of the LEDs used in the Experiment section.

The shaved back skin of each of three beagle dogs (2-11 years old) was irradiated with three LED lights with respective peak wavelengths of 310, 320, and 330 nm. FIG. 4 shows the emission spectra of the LEDs used. Specifically, the LED light with a peak wavelength of 310 nm was irradiated once a day at a fluence of 300 mJ/cm² for a total of 4 days or once at a fluence of 1500 mJ/cm². The LED light with a peak wavelength of 320 nm or 330 nm was irradiated once a day at a fluence of 300 mJ/cm² for a total of four days.

In these exemplary experiments, wavelength determination was carried out by measuring the emission spectrum using multichannel detector (model: PMA-11 C7473; Hamamatsu Photonics K.K.). The irradiance (mW/cm²) was measured using a photodiode sensor (model: PD300-UV; Ophir), the sensitivity of which had been calibrated at the peak wavelength of the LED used. The fluence (mJ/cm²) was calculated as a product of irradiance (mW/cm²) and irradiation time (sec).

Skin tissue samples were collected from the skin around the center of the irradiated area and from the skin in the non-irradiated area by using a biopsy trepan (BP-80F, Kai medical). The skin tissue samples obtained were incubated with RNAlater® (Thermo Fisher Scientific Inc.) at 4° C. overnight and then stored at −80° C. until use.

Total RNA was crudely extracted from the thawed skin tissue samples using RNAisoPlus (MACHEREY-NAGEL GmbH & Co.), and purified using NucleoSpin® RNA Clean-up XS (MACHEREY-NAGEL GmbH & Co.).

RNA-seq analysis (Takara Bio Inc.) was carried out on the purified total RNA. Briefly, poly A⁺ RNA was isolated from the total RNA, and fragmented. The resulting RNA fragments were used as templates for reverse transcription reaction to synthesize single-stranded cDNAs, which were then used as templates to synthesize double-stranded cDNAs in the presence of dUTP. The both ends of the obtained (dUTP-incorporated) double-stranded cDNAs were blunted and phosphorylated, and then ligated with indexed adaptors with 3'-dA overhang. The resulting adapter-ligated double-stranded cDNAs were used as templates for PCR amplification using a polymerase that does not amplify dUTP-incorporated DNAs. The amplified cDNA fragments were used as a sequence library. For sequence analysis, the sequencer NovaSeq system (Illumina, Inc.) was used. Information was analyzed about only known genes.

Except for the genes for which FPKM (Fragments Per Kilobase of transcript per Million fragments sequenced) or count values were zero for all the skin tissue samples, the genes were extracted for which FPKM and/or count values were significantly changed in the irradiated area relative to the non-irradiated area for each irradiation condition (p≤0.01; t-test).

Figure 5:
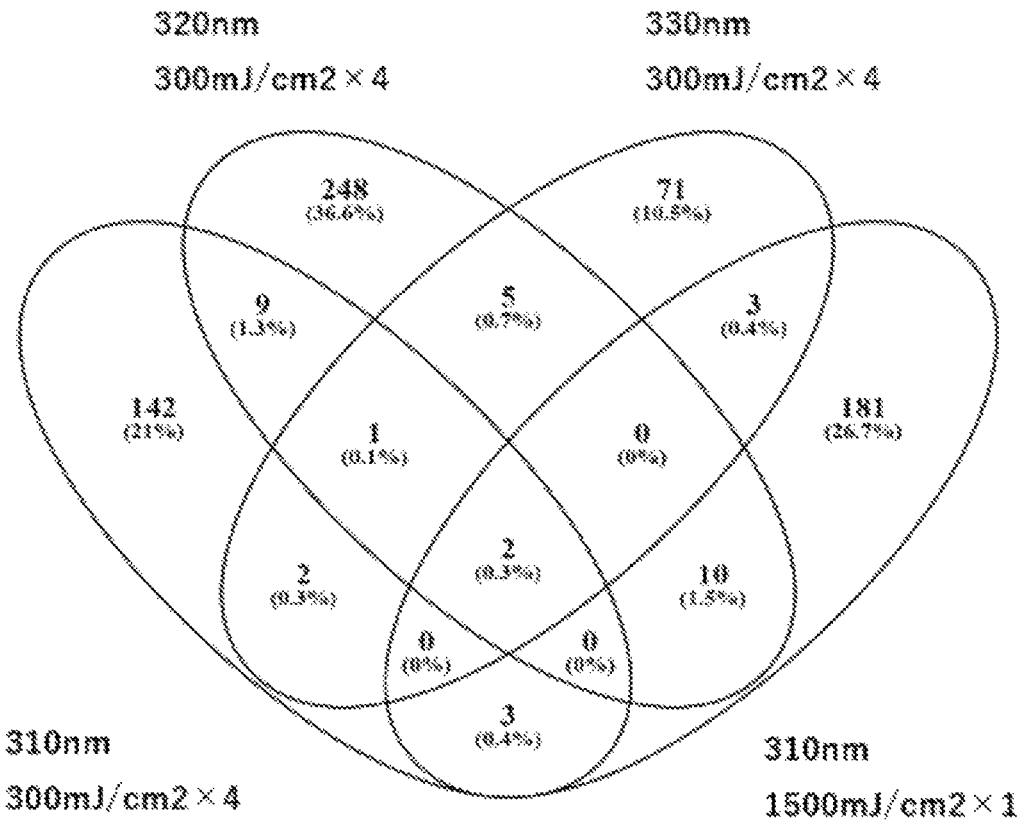
FIG. 5 is a Venn diagram showing the number of genes with increased expression under the respective irradiation conditions.
Figure 6A:
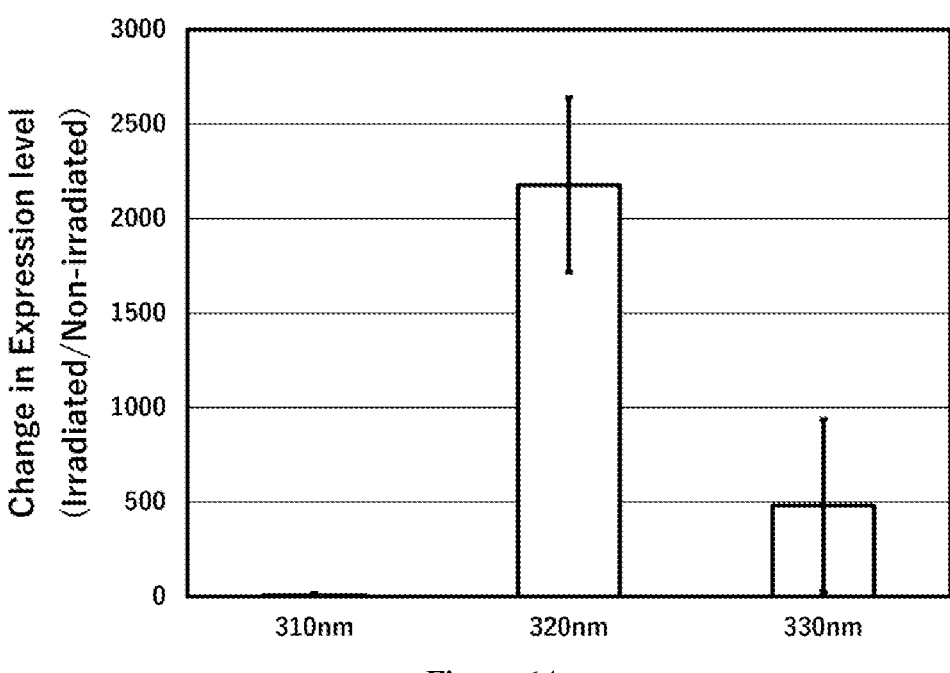
FIG. 6A illustrates changes in the expression level of a DHPR VGCC gene (CACNG1) by irradiation with different wavelengths of LED light. The changes are expressed as ratio of (expression level in irradiated cells)/(expression level in unirradiated cells).
Figure 6B:
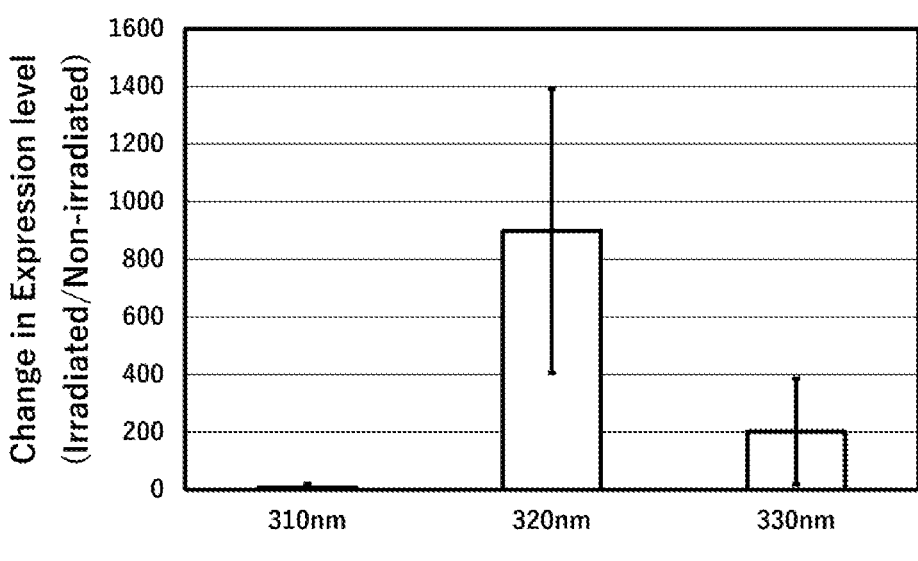
FIG. 6B illustrates changes in the expression level of a DHPR VGCC gene (CACNG6) by irradiation with different wavelengths of LED light.
Figure 6C:
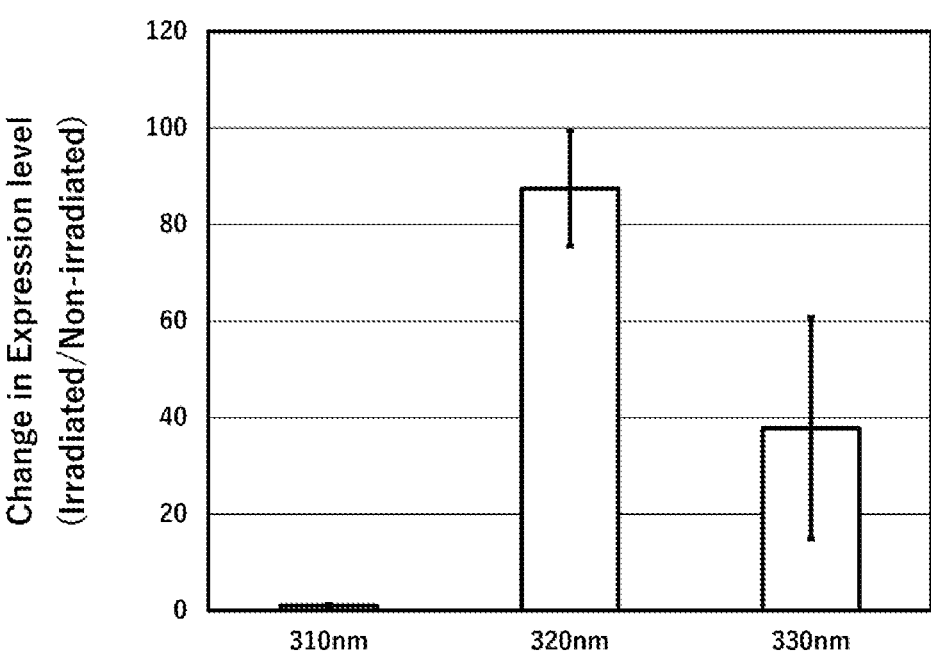
FIG. 6C illustrates changes in the expression level of an SERCA gene (ATP2A1) by irradiation with different wavelengths of LED light.
Figure 6D:
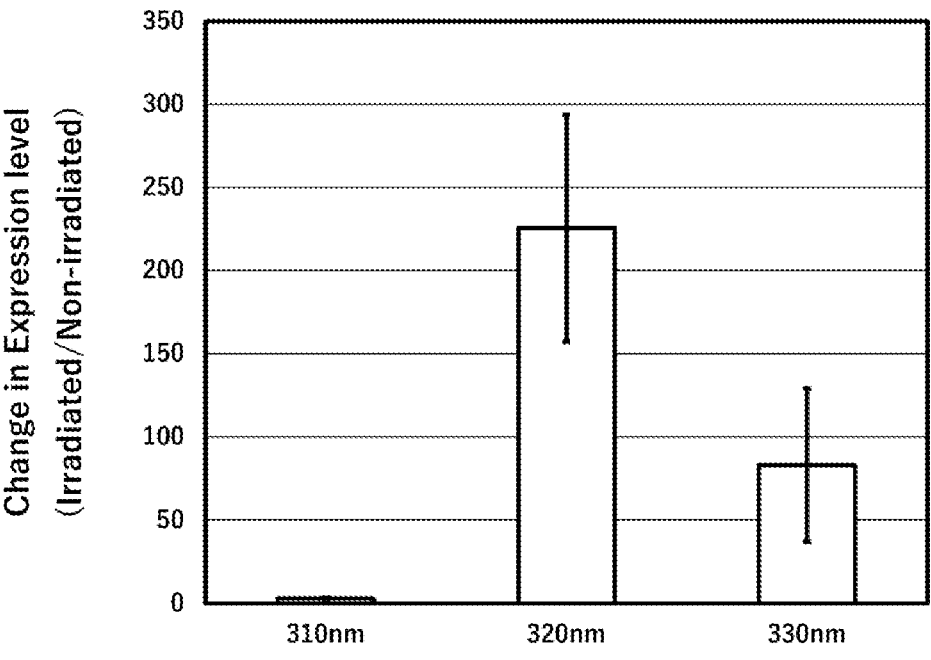
FIG. 6D illustrates changes in the expression level of an RYP gene (RYR1) by irradiation with different wavelengths of LED light.
Figure 6E:
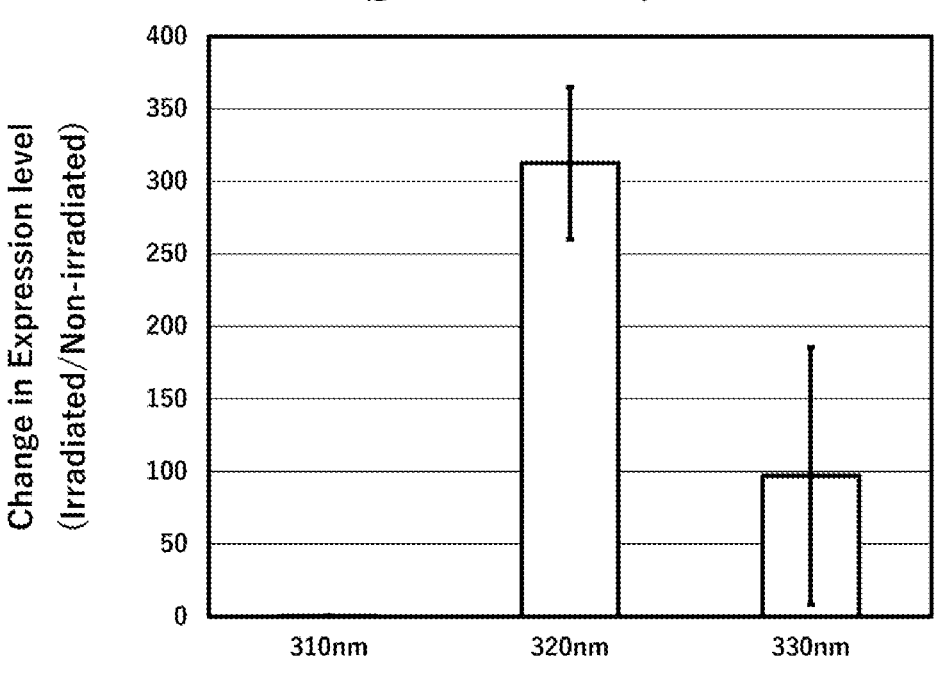
FIG. 6E illustrates changes in the expression level of a TRDN gene (TRDN) by irradiation with different wavelengths of LED light.
Figure 6F:
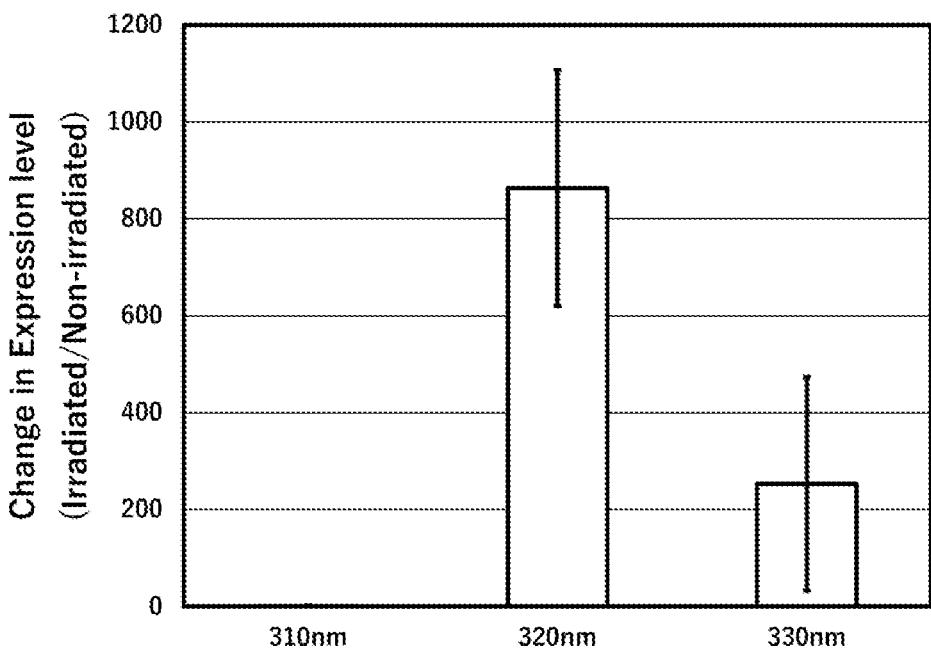
FIG. 6F illustrates changes in the expression level of a CASQ gene (CASQ1) by irradiation with different wavelengths of LED light.
Figure 6G:
FIG. 6G illustrates changes in the expression level of a CASQ gene (CASQ2) by irradiation with different wavelengths of LED light.
Figure 6G:
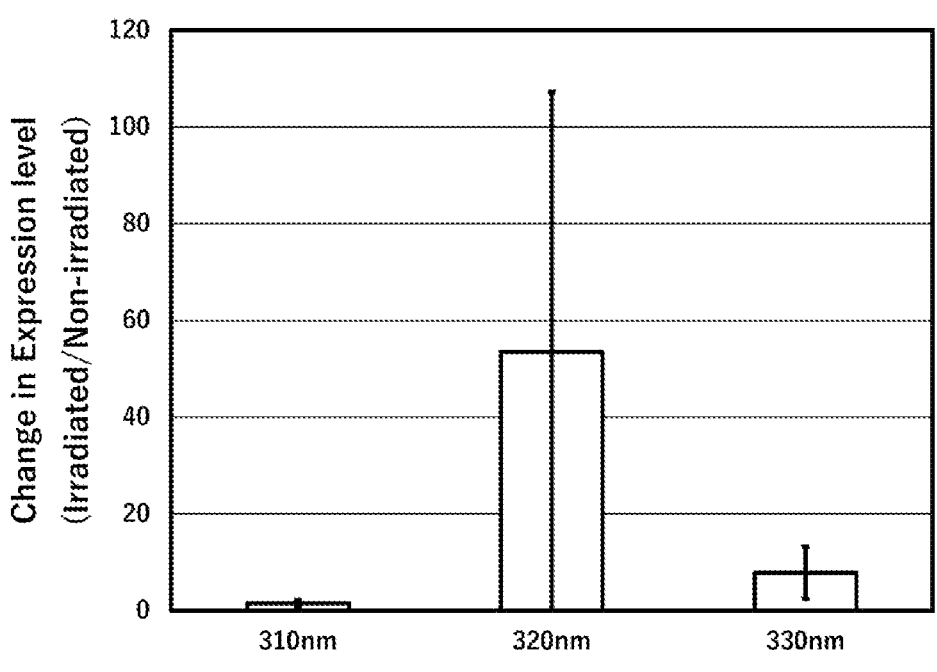
Figure 6H:
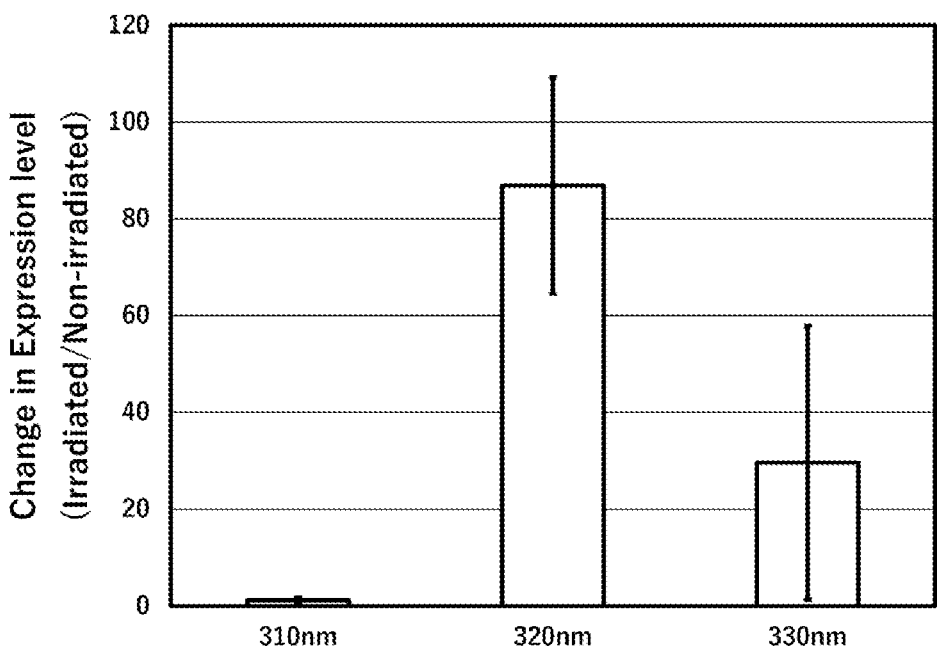
FIG. 6H illustrates changes in the expression level of a HRC gene (HRC) by irradiation with different wavelengths of LED light.
Figure 6I:
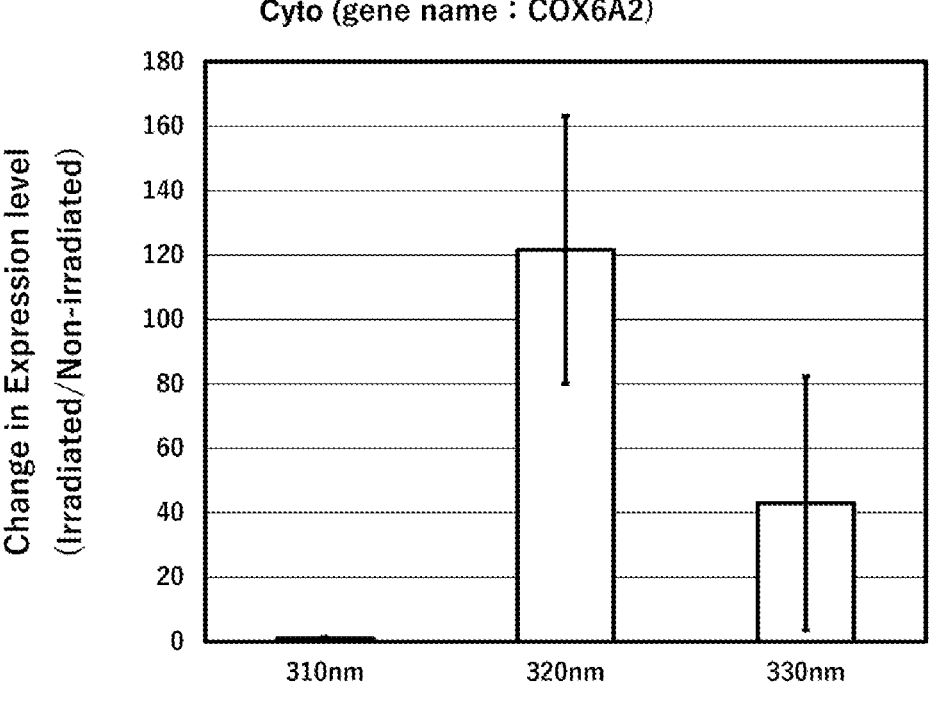
FIG. 6I illustrates changes in the expression level of a Cyto gene (COX6A2) by irradiation with different wavelengths of LED light.

FIG. 5 is a Venn diagram showing the number of genes with changed expression under the respective irradiation conditions. The Venn diagram was created using Venny (BioinfoGP). As can be seen from FIG. 5, the expression of 248 genes was specifically changed by the irradiation of light with a peak wavelength at about 320 nm. Therefore, it is inferred that the expression of certain genes can be controlled by irradiation of light with a peak wavelength of about 320 nm.

The extracted genes were then subjected to Pathway analysis and Gene Ontology (GO) analysis using DAVID 6.8 (NIAID) analysis software. In the pathway analysis, the genes were classified according to the Pathway database. In the GO analysis, the genes were analyzed for Biological Process (BP).

The pathway analysis extracted the pathways that were significantly altered under respective irradiation conditions (p≤0.05). The results are shown in Table 1.

TABLE 1

| Term | p value | | | |
| | 310 nm 300 mJ/ cm2 × 4 | 320 nm 300 mJ/ cm2 × 4 | 320 nm 300 mJ/ cm2 × 4 | 310 nm 1500 mJ/ cm2 × 4 |
| --- | --- | --- | --- | --- |
| Purine metabolism | 1.3E−02 | — | — | — |
| Aminoacyl-tRNA biosynthesis | 5.0E−02 | — | — | — |
| Calcium signaling pathway | — | 1.3E−03 | — | — |
| Cardiac muscle contraction | — | 1.6E−03 | — | — |
| Glycolysis/Gluconeogenesis | — | 6.7E−03 | — | — |
| Biosynthesis of amino acids | — | 1.1E−02 | — | — |
| Carbon Metabolism | — | 1.1E−02 | — | — |
| Biosynthesis of antibiotics | — | 1.4E−02 | — | — |
| Insulin signaling pathway | — | 2.3E−02 | — | — |
| Adrenergic signaling in cardiomyocytes | — | 2.3E−02 | — | — |
| Glucagon signaling pathway | — | 2.9E−02 | — | — |
| Oxytocin signaling pathway | — | 3.1E−02 | — | — |
| Metabolic pathways | — | — | 2.7E−02 | — |
| RNA transport | — | — | 3.3E−02 | — |
| beta-Alanine metabolism | — | — | — | 4.5E−02 |

The increase or decrease in gene expression was closely examined. The direction of change in the extracted pathways is summarized below:

(a) By irradiation of LED light with a peak wavelength of 310 nm at a dose of 300 mJ/cm$^2$ once a day for a total of 4 days:

Purine metabolism: The movement of ATP-related compounds and synthesis of urates are promoted;

Aminoacyl-tRNA biosynthesis: Glycine synthesis is promoted and histidine and phenylalanine synthesis is suppressed;

(b) By irradiation of LED light with a peak wavelength of 320 nm at a dose of 300 mJ/cm$^2$ once a day for a total of 4 days:

Calcium signaling pathway: Ca$^{2+}$ uptake into the endoplasmic reticulum is promoted and muscle contraction and glycogenolysis are promoted;

Cardiac muscle contraction pathway: Intracellular Ca$^{2+}$ uptake is promoted and cytochrome c oxidase and myosin are activated;

Glycolysis/Gluconeogenesis: Glycolysis/Gluconeogenesis are activated;

Biosynthesis of amino acids: Amino acid biosynthesis is activated;

Carbon metabolism: Carbon metabolism is activated;

Biosynthesis of antibiotics: Antibiotic biosynthesis is activated;

Insulin signaling pathway: Glycogen synthesis is suppressed and glycolysis is promoted;

Adrenergic signaling in cardiomyocytes: Intracellular Ca$^{2+}$ uptake is promoted and myosin is activated;

Glucagon signaling pathway: Glycogenolysis is promoted;

Oxytocin signaling pathway: Intracellular Ca$^{2+}$ uptake and Ca$^{2+}$ efflux from the endoplasmic reticulum are prompted.

(c) By irradiation of LED light with a peak wavelength of 330 nm at a dose of 300 mJ/cm$^2$ once a day for a total of 4 days:

Metabolic pathways: Metabolism is activated;

RNA transport: RNA transport from nucleus to cytoplasm is suppressed.

(d) By a single irradiation of LED light with a peak wavelength of 310 nm at a dose of 1500 mJ/cm$^2$.

beta-Alanine metabolism: beta-alanine metabolism is suppressed.

In the pathway analysis in (b) above, the hit genes and fold changes in expression for each pathway are shown in Tables 2-11 below. The fold changes in expression is calculated as $\log_2$([FPKM value for the irradiated area]/[FPKM value for the non-irradiated area]).

TABLE 2

| Calcium signaling pathway | | | |
| Gene Name | ENTREZ_GENE_ID | Fold change | Related Protein |
| --- | --- | --- | --- |
| troponin C2, fast skeletal type(TNNC2) | 485899 | 8.3 | TnC |
| ryanodine receptor 1(RYR1) | 606491 | 7.8 | RYR |
| ATPase sarcoplasmic/endoplasmic reticulum Ca2+ transporting 1(ATP2A1) | 479797 | 6.5 | SEPCA |
| 5-hydroxytryptamine receptor 2A(HTRA2) | 403882 | 6.5 | GPCR |
| phosphorylase kinase catalytic subunit gamma 1(PHKG1) | 489784 | 2.6 | PHK |
| voltage dependent anion channel 3(VDAC3) | 606963 | 0.5 | VDAC |
| purinergic receptor P2X 4(P2RX4) | 448783 | 0.1 | ROC |
| calmodulin like 5(CALML5) | 487146 | −0.3 | CALM |
| cholinergic receptor muscarinic 5(CHRM5) | 487472 | −3.3 | GPCR |

TABLE 3

| | Cardiac muscle contraction | | |
|---|---|---|---|
| Gene Name | ENTREZ_GENE_ID | Fold change | Related Protein |
| calcium voltage-gated channel auxil-iary subunit gamma 1(CACNG1) | 610892 | 11.8 | DHPR |
| calcium voltage-gated channel auxil-iary subunit gamma 6(CACNG6) | 484315 | 10.4 | DHPR |
| ATPase Na+/K+ transporting family member beta 4(ATP1B4) | 481036 | 10.2 | ATP |
| cytochrome c oxidase subunit VIa polpypeptide 2(COX6A2) | 479780 | 6.9 | Cyto |
| myosin heavy chain 7(MYH7) | 403807 | 1.7 | Myosin |
| calcium voltage-gated channel auxil-iary subunit beta 1(CACNB1) | 491030 | 0.6 | DHPR |

TABLE 4

| | Glycolysis/Gluconeogenesis | | |
|---|---|---|---|
| Gene Name | ENTREZ_GENE_ID | Fold change | Related Protein |
| phosphoglycerate mutase 2(PGAM2) | 475495 | 10.0 | EC 5.4.2.11 |
| enolase 3(ENO3) | 479469 | 5.0 | EC 4.2.1.11 |
| fructose-1,6-biphosphatase isozyme 2(LOC476300) | 476300 | 2.8 | EC 3.1.3.11 |
| phosphofructokinase, muscle(PFKM) | 403849 | 1.8 | EC 2.7.1.11 |
| enolase 2(ENO2) | 100856683 | −0.3 | EC 4.2.1.11 |

TABLE 5

| | Biosynthesis of amino acids | |
|---|---|---|
| Gene Name | ENTREZ_GENE_ID | Fold change |
| phosphoglycerate mutase 2(PGAM2) | 475495 | 10.0 |
| enolase 3(ENO3) | 479469 | 5.0 |
| phosphotructokinase, muscle(PFKM) | 403849 | 2.8 |
| glutamic-oxaloacetic transaminase 2(GOT2) | 478103 | 1.9 |
| enolase 2(ENO2) | 100856683 | −0.3 |

TABLE 6

| | Carbon metabolism | |
|---|---|---|
| Gene Name | ENTREZ_GENE_ID | Fold change |
| phosphoglycerate mutase 2(PGAM2) | 475495 | 10.0 |
| enolase 3(ENO3) | 479469 | 5.0 |
| fructose-1,6-bisphosphatase isozyme 2(LOC476300) | 476300 | 2.8 |
| phosphotructokinase, muscle(PFKM) | 403849 | 1.9 |
| glutamic-oxaloacetic transaminase 2(GOT2) | 478103 | 0.4 |
| enolase 2(ENO2) | 100856683 | −0.3 |

TABLE 7

| Biosynthesis of antibiotics | | |
| --- | --- | --- |
| Gene Name | ENTREZ_GENE_ID | Fold change |
| phosphoglycerate mutase 2(PGAM2) | 475495 | 10.0 |
| adenosine monophosphate deaminase 1(AMPD1) | 606901 | 5.5 |
| enolase 3(ENO3) | 479469 | 5.0 |
| fructose-1,6-bisphosphatase isozyme 2(LOC476300) | 476300 | 2.8 |
| phosphotructokinase, muscle(PFKM) | 403849 | 1.9 |
| Carboxymethylenebutenolidase homolog(CMBL) | 478619 | 0.9 |
| glutamic-oxaloacetic transaminase 2(GOT2) | 478103 | 0.4 |
| enolase 2(ENO2) | 100856683 | −0.3 |

TABLE 8

| Insulin signaling pathway | | | |
| --- | --- | --- | --- |
| Gene Name | ENTREZ_GENE_ID | Fold change | Related Protein |
| protein phosphatase regulatory subunit 3A(PPP1R3A) | 482411 | 10.1 | PP1 |
| phosphorylase, glycogen, muscle(PYGM) | 611078 | 8.0 | PYG |
| fructose-1,6-biphosphatase isozyme 2(LOC476300) | 476300 | 2.8 | FBP |
| phosphorylase kinase catalytic subunit gamma 1(PHKG1) | 489784 | 2.6 | PHK |
| phosphorylase, glycogen, liver(PYGL) | 403738 | −0.1 | PYG |
| calmodulin like 5(CLAML5) | 487146 | −0.3 | PHK |

TABLE 9

| Adrenergic signaling in cardiomyocytes | | | |
| --- | --- | --- | --- |
| Gene Name | ENTREZ_GENE_ID | Fold change | Related Protein |
| calcium voltage-gated channel auxiliary sub-unit gamma 1(CACNG1) | 610892 | 11.8 | DHPR |
| calcium voltage-gated channel auxiliary sub-unit gamma 6(CACNG6) | 484315 | 10.4 | DHPR |
| ATPase Na+/K+ transporting family member beta 4(ATP1B4) | 481036 | 10.2 | INaK |
| myosin heavy chain 7(MYH7) | 403807 | 1.7 | Myosin |
| calcium voltage-gated channel auxiliary sub-unit beta 1(CACNB1) | 491030 | 0.6 | DHPR |
| calmodulin like 5(CALML5) | 487146 | −0.3 | CaM |

TABLE 10

| Glucagon signaling pathway | | | |
| --- | --- | --- | --- |
| Gene Name | ENTREZ_GENE_ID | Fold change | Related Protein |
| phosphoglycerate mutase 2(PGAM2) | 475495 | 10.0 | PGM |
| phosphorylase, glycogen, muscle(PYGM) | 611078 | 8.0 | PYGL |
| phosphorylase kinase catalytic subunit gamma 1(PHKG1) | 489784 | 2.6 | PHK |
| phosphorylase, glycogen, liver, PYGL | 403738 | −0.1 | PYGL |
| calmodulin like 5(CALML5) | 487146 | −0.3 | CALM |

TABLE 11

| Oxytocin signaling pathway | | | |
| --- | --- | --- | --- |
| Gene Name | ENTREZ_GENE_ID | Fold change | Related Protein |
| calcium voltage-gated channel auxiliary subunit gamma 1(CACNG1) | 610892 | 11.8 | VGCC |
| calcium voltage-gated channel auxilary subunit gamma 6(CACNG6) | 484315 | 10.4 | VGCC |
| ryanodine receptor 1(RYR1) | 606491 | 7.8 | RYR |
| potassium voltage-gated channel subfamily J member 12(KCNJ12) | 403760 | 2.0 | GIRK |
| calcium voltage-gated channel auxiliary subunit beta 1(CACNB1) | 491030 | 0.6 | VGCC |
| calmodulin like 5(CALML5) | 487146 | −0.3 | CALM |

As can be seen from Table 2, it was observed that the gene expression was significantly increased for TnC (cardiac troponin C), RYR (ryanodine receptor), SERCA (sarcoplasmic reticulum calcium ATPase), GPCR (G protein-coupled receptor), PHK (phosphorylase kinase), VDAC (voltage-dependent anion channel), and ROC (receptor-activated calcium channel).

Therefore, it can be understood that the irradiation of light with a peak wavelength of about 320 nm can promote $Ca^{2+}$ uptake into the endoplasmic reticulum, muscle contraction, and glycogenolysis, in the Calcium signaling pathway.

As can be seen from Table 3, it was observed that the gene expression was significantly increased for DHPR (dihydropyridine receptor), ATP (ATP synthase), Cyto (cytochrome c oxidase), and Myosin (myosin).

Therefore, it can be understood that the irradiation of light with a peak wavelength of about 320 nm can promote intracellular $Ca^{2+}$ uptake and activate cytochrome c oxidase and myosin, in the Cardiac muscle contraction pathway.

As can be seen from Table 4, it was observed that the gene expression was significantly increased for EC 5.4.2.11 (phosphoglycerate mutase), EC 4.2.1.11 (phosphopyruvate hydratase), EC 3.1.3.11 (fructose-bisphosphatase), and EC 2.7.1.11 (6-phosphofructokinase).

Therefore, it can be understood that the irradiation of light with a peak wavelength of about 320 nm can activate the glycolysis/gluconeogenesis in the Glycolysis/Gluconeogenesis pathway.

As can be seen from Table 5, it was observed that the gene expression was significantly increased for phosphoglycerate mutase 2 (PGAM2), enolase 3 (ENO3), phosphofructokinase, muscle (PFKM), and glutamic-oxaloacetic transaminase 2 (GOT2).

Therefore, it can be understood that the irradiation of light with a peak wavelength of about 320 nm can activate the biosynthesis of amino acids, in the Biosynthesis of amino acids pathway.

As can be seen from Table 6, it was observed that the gene expression was significantly increased for phosphoglycerate mutase 2 (PGAM2), enolase 3 (ENO3), fructose-1,6-bisphosphatase isozyme 2 (LOC476300), phosphofructokinase, muscle (PFKM), and glutamic-oxaloacetic transaminase 2 (GOT2).

Therefore, it can be understood that the irradiation of light with a peak wavelength of about 320 nm can activate carbon metabolism in the Carbon metabolism pathway.

As can be seen from Table 7, it was observed that the gene expression was significantly increased for phosphoglycerate mutase 2 (PGAM2), adenosine monophosphate deaminase 1 (AMPD1), enolase 3 (ENO3), fructose-1,6-bisphosphatase isozyme 2 (LOC476300), phosphofructokinase, muscle (PFKM), carboxymethylenebutenolidase homolog (CMBL), and glutamic-oxaloacetic transaminase 2 (GOT2).

Therefore, it can be understood that the irradiation of light with a peak wavelength of about 320 nm can activate the biosynthesis of antibiotics in the Biosynthesis of antibiotics pathway.

As can be seen from Table 8, it was observed that the gene expression was significantly increased for PP1 (protein phosphatase 1), PYG (glycogen phosphorylase), FBP (fructose-1,6-bisphosphatase), and PHK (phosphorylase kinase).

Therefore, it can be understood that the irradiation of light with a peak wavelength of about 320 nm can suppress glycogen synthesis and promote glycolysis in the Insulin signaling pathway.

As can be seen from Table 9, it was observed that the gene expression was significantly increased for DHPR (dihydropyridine receptor), InaK ($Na^+/K^+$-ATPase), and Myosin (myosin).

Therefore, it can be understood that the irradiation of light with a peak wavelength of about 320 nm can promote intracellular $Ca^{2+}$ uptake and activate myosin in the Adrenergic signaling pathway in cardiomyocytes.

As can be seen from Table 10, it was observed that the gene expression was significantly increased for PGM (phosphoglycerate mutase), PYGL (glycogen phosphorylase), and PHK (phosphorylase kinase).

Therefore, it can be understood that the irradiation of light with a peak wavelength of about 320 nm can promote glycogenolysis in the Glucagon signaling pathway.

As can be seen from Table 11, it was observed that the gene expression was significantly increased for VGCC (voltage-gated calcium channel), RYR (ryanodine receptor), and GIRK (G-protein-activated inwardly rectifying potassium channel).

Therefore, it can be understood that the irradiation of light with a peak wavelength of about 320 nm can promote intracellular $Ca^{2+}$ uptake and $Ca^{2+}$ efflux from the endoplasmic reticulum in the Oxytocin signaling pathway.

In the GO analysis, it was observed that the irradiation of light with a peak wavelength of about 320 nm caused a significant change in several Biological Processes (Table 12), which are processes seen in muscle tissues. These changes are caused by the effects of inducing expression of calcium channel and/or calcium pump in cells.

TABLE 12

| Term | Counts | p value |
| --- | --- | --- |
| skeletal muscle fiber development | 7 | 2.40E−07 |
| skeletal muscle contraction | 6 | 2.70E−06 |

TABLE 12-continued

| Term | Counts | p value |
|---|---|---|
| muscle contraction | 6 | 5.20E–05 |
| positive regulation of skeletal muscle fiber development | 4 | 1.10E–04 |
| glycogen catabolic process | 4 | 2.60E–04 |
| skeletal muscle cell differentiation | 6 | 4.30E–04 |
| positive regulation of myoblast fusion | 4 | 1.10E–03 |
| positive regulation of myoblast differentiation | 4 | 1.90E–03 |
| sarcomere organization | 4 | 3.10E–03 |
| cardiac muscle tissue morphogenesis | 3 | 5.90E–03 |
| cellular response to estradiol stimulus | 3 | 2.00E–02 |
| negative regulation of ERK1 and ERK2 cascade | 4 | 2.20E–02 |
| regulation of heart rate | 3 | 3.20E–02 |
| ATP metabolic process | 3 | 3.90E–02 |
| muscle filament sliding | 2 | 4.40E–02 |
| detection of muscle stretch | 2 | 4.40E–02 |

The calcium signaling pathway-related genes, whose expression levels were specifically increased by the irradiation of light with a peak wavelength of about 320 nm, include DHPR, VGCC, SERCA, RYR, TRDN, CASQ, HRC and Cyto. FIGS. 6(A)-(I) show the changes in expression levels by the irradiation of light with respective peak wavelengths. From the data shown in the figures, it can be understood that the irradiation of light with a peak wavelength of about 320 nm upregulate specifically the expression of DHPR, VGCC, SERCA, RYR, TRDN, CASQ, HRC and Cyto (at least about 30-fold).

Altogether, the irradiation of cells with light at a peak wavelength of about 320 nm can modulate calcium signaling pathway, insulin signaling pathway, adrenergic signaling pathway in cardiomyocytes, glucagon signaling pathway, or oxytocin signaling pathway; control muscle contraction, neuronal transmission, mitochondrial activity or cell death (or apoptosis); activate glycolysis/glycogenesis, amino acid biosynthesis, carbon metabolism or antibiotic biosynthesis; and promote glycogenolysis, and/or osteoblast-like differentiation.

The method and apparatus of the present disclosure are expected to be applicable to the following applications.
(1) Regenerative Medicine for Bones and Teeth Progenitor cells, such as mesenchymal stem cells and osteoblasts, are known to take up calcium ions to produce bone cells. Therefore, it can be expected that the method and apparatus of the present disclosure can be applied as a method for efficiently inducing progenitor cells to differentiate into bone cells ex vivo, and therefore as a method for producing graft (bone) materials containing cultured bone cells. It is also expected that the method of the present disclosure can be applied as a method for efficiently inducing differentiation into bone cells of progenitor cells grafted into a patient.
(2) Improvement in Barrier Function of Skin and Mucosa The method and apparatus of the present disclosure can be expected to promote the uptake of calcium ions by epidermal cells. It is known that promoted uptake of calcium ions by epidermal cells leads to activation of epidermal transglutaminase (Tgase) and cross-linking of proteins in the cells, resulting in skin formation. Therefore, the method of the present disclosure can be expected to promote skin formation, increase the physical strength of skin and mucosa, and enhance the moisturizing function.

Because it was observed that the irradiation of light in a wavelength range of 315-325 nm induced the expression of genes such as FGF6 (fibroblast growth factor 6), MYOD1 (myoblast determination protein 1), and MYOG (myogenic factor 4), the light irradiation method of the present disclosure can be expected to have the effect of promoting collagen synthesis in fibroblasts, thereby providing skin beautifying effect.
(3) Research and Treatment of Nervous and Muscular Diseases Many researches have been conducted on calcium ion signaling in relation to neurotransmission and muscle control. Currently, calcium ion signaling can be modulated by using calcium ionophores (agents to increase the permeability of calcium ions to cell membranes), photogenetics (in the target cell that have been engineered to express photoactivated ion channels such as channel rhodopsin, calcium ion signaling can be controlled by irradiating with specific light wavelengths), and other methods. By the method and apparatus of the present disclosure, calcium ion signaling can be modulated by light irradiation alone, which is simple and can be closer to clinical applications.

It is known that the regulation of muscle contraction is controlled by changing intracellular calcium ion concentration. The method and apparatus of the present disclosure can be expected to be applied to cardiomyocyte culture for regenerative medicine.

It has also been reported that in some neurological diseases, such as Alzheimer's disease and Parkinson's disease, the manner of changes in intracellular calcium ion concentration are different from that in normal conditions. The method and apparatus of the present disclosure are expected to be useful for elucidating the mechanisms and proposing treatments such as nerve regeneration.
(4) Infertility It is also known that calcium ions have effects on infertility. For example, sperm are known to induce a change in motility of flagella and cilia by transiently increasing intracellular calcium ion concentration due to the influx of calcium ions, followed by decreasing intracellular calcium ion concentration due to the efflux of calcium ions. It is also known that by increasing the intracellular calcium ion concentration, sperm undergo capacitation and an acrosome reaction to enter oocyte. Therefore, the method and apparatus of the present disclosure can be used to control sperm motility, which is an important parameter of sperm function, and an acrosome reaction. In other words, the methods and apparatus of the present disclosure can be expected to improve the motility of sperm that are unable to enter an oocyte due to their weak ability to control calcium ions.

In addition, the method and apparatus of the present disclosure are expected to activate oocyte and improve the fertilization rate. For example, it is believed that a reason for failed fertilization after intracytoplasmic sperm injection (ICSI) is lack of oocyte activation, which leads to an insufficient increase of calcium ions induced by sperm-oocyte fusion. As prior art, calcium ionophores are used to increasing the permeability of calcium ions to oocyte cell membrane, thereby activating oocyte. However, the method and apparatus of the present disclosure can activate oocyte more simply.

A fertilized egg periodically changes the intracellular concentration of calcium ions over a long period of time. This is known as calcium ion oscillation, and it affects embryonic development. Specifically, it is known that disturbed oscillation causes abnormal gene expression and a decrease in the normal birth rate. The method and apparatus of the present disclosure are expected to control the intracellular calcium ion concentration, thereby increasing the normal birth rate.

(5) Induction of Cell Apoptosis

There are conventional techniques for removing unwanted cells from biological tissues and cultured cells, including ablation by laser irradiation and apoptosis induction techniques by overload calcium ions (uptake of excess calcium ions) using calcium ionophores such as ionomycin. The method and apparatus of the present disclosure can induce locally apoptosis of unwanted cells by light irradiation at low intensity with less heat generation, and is expected to remove only unwanted cells without causing heat or light damage to normal cells.

What is claimed is:

1. A method of inducing gene expression of a calcium channel and/or a calcium pump in a cell, the method comprising:
   irradiating the cell with light in a wavelength range of 315-325 nm,
   wherein the calcium channel and/or the calcium pump is/are at least one selected from the group consisting of dihydropyridine receptor (DHPR), voltage-gated calcium channel (VGCC), ryanodine receptor (RYR), and sarcoendoplasmic reticulum $Ca^{2+}$-ATPase (SERCA).

2. The method according to claim 1, wherein in the step of irradiating, the cell is not irradiated with light at any wavelength of 330-400 nm, or is irradiated with light in wavelengths of 330-400 nm at a fluence that is less than 50% of that of the light in the wavelength range of 315-325 nm.

3. The method according to claim 1, wherein in the step of irradiating, the cell is not irradiated with light at any wavelength of 200-300 nm, or is irradiated with light in wavelengths of 200-300 nm at a fluence that is less than 30% of that of the light in the wavelength range of 315-325 nm.

4. The method according to claim 1, wherein the light in the wavelength range of 315-325 nm has a wavelength spectrum with a peak wavelength at 320±5 nm and a full width at half maximum in a range of 1-20 nm.

5. The method according to claim 1, wherein the light in the wavelength range of 315-325 nm is emitted by a light-emitting diode (LED).

6. The method according to claim 1, wherein the cell is an excitatory cell.

7. A method of modulating calcium signaling in a cell, the method comprising:
   inducing gene expression of a calcium channel and/or a calcium pump in the cell by applying the method according to claim 1 to the cell; and
   measuring a physiological event involving calcium signaling in the cell.

8. The method according to claim 7, wherein the physiological event is one or more selected from the group consisting of muscle contraction, neuronal transmission, cell death, and osteoblast-like differentiation.

9. A method of making a cell having induced gene expression of a calcium channel and/or a calcium pump, comprising:
   irradiating a cell with light in a wavelength range of 315-325 nm; and
   freezing the irradiated cell,
   wherein, in the step of irradiating:
      the cell is not irradiated with light at any wavelength of 200-300 nm, or is irradiated with light in wavelengths of 200-300 nm at a fluence that is less than 30% of that of the light in the wavelength range of 315-325 nm, and
      the cell is not irradiated with light at any wavelength of 330-400 nm, or is irradiated with light in wavelengths of 330-400 nm at a fluence that is less than 50% of that of the light in the wavelength range of 315-325 nm.

10. The method of claim 1, wherein the light in the wavelength range of 315-325 nm has a fluence of 50-4,500 $mJ/cm^2$.

* * * * *